US007598080B2

(12) United States Patent
Deirmengian

(10) Patent No.: US 7,598,080 B2
(45) Date of Patent: Oct. 6, 2009

(54) DIAGNOSTIC ASSAY FOR SOURCE OF INFLAMMATION

(76) Inventor: Carl Deirmengian, 1 W. Superior St., 1 W. Superior Pl., Apartment 1909, Chicago, IL (US) 60610

( * ) Notice: Subject to any disclaimer, the term of this patent is extended or adjusted under 35 U.S.C. 154(b) by 210 days.

(21) Appl. No.: 11/200,446

(22) Filed: Aug. 9, 2005

(65) Prior Publication Data

US 2006/0040301 A1   Feb. 23, 2006

Related U.S. Application Data

(60) Provisional application No. 60/603,313, filed on Aug. 20, 2004.

(51) Int. Cl.
*C12N 15/85* (2006.01)
*C12Q 1/68* (2006.01)
*C12P 21/00* (2006.01)
*C12N 15/63* (2006.01)

(52) U.S. Cl. .......................... 435/325; 435/6; 435/70.1
(58) Field of Classification Search ....................... None
See application file for complete search history.

(56) References Cited

U.S. PATENT DOCUMENTS

| | | | |
|---|---|---|---|
| 4,366,241 | A | 12/1982 | Tom et al. |
| 4,376,110 | A | 3/1983 | David et al. |
| 4,517,288 | A | 5/1985 | Giegel et al. |
| 4,837,168 | A | 6/1989 | De Jaeger et al. |
| 5,143,854 | A | 9/1992 | Pirrung et al. |
| 5,800,992 | A | 9/1998 | Fodor et al. |
| 5,837,832 | A | 11/1998 | Chee et al. |
| 5,953,727 | A | 9/1999 | Akerblom et al. |
| 6,365,352 | B1 | 4/2002 | Yerramilli |
| 2003/0077611 | A1 | 4/2003 | Slepnev |
| 2003/0082512 | A1 | 5/2003 | Yerramilli |
| 2005/0037344 | A1 | 2/2005 | Stuhlmuller et al. |
| 2006/0294604 | A1* | 12/2006 | Fridman et al. ............... 800/14 |

FOREIGN PATENT DOCUMENTS

WO   WO 93/09668   5/1993
WO   WO 99/32660   7/1999

OTHER PUBLICATIONS

Stratagene 1988 catalog.*
Yum et al. Involvement of Phosphoinositide 3_Kinases in Neutrophil Activation and the Development of Acute Lung Injury. J. Immunology 161: 6601-6608, 2001.*
Altschul, et al., "Issues in searching molecular sequence databases", *Nature Genet.*, 6:119-129 (1994).
Altschul, "A protein alignment scoring system sensitive at all evolutionary distances", *J. Mol. Evol.*, 36:290-300 (1993).
Golub, et al., "Molecular classification of cancer: class discovery and class prediction by gene expression monitoring", *Science*, 286(5439):531-7 (1999).

Henikoff and Henikoff, "Amino acid substitution matrices from protein blocks", *Proc. Natl. Acad. Sci. USA*, 89:10915-10919 (1992).
Huse, et al., "Generation of a large combinatorial library of the immunoglobulin repertoire in phage lambda", *Science*, 246:1275-1281 (1989).
Jungblut and Thiede, "Protein identification from 2-DE gels by MALDI mass spectrometry", *Mass Spectr. Rev.*, 16:145-162 (1997).
Karlin, et al., "Methods for assessing the statistical significance of molecular sequence features by using general scoring schemes", *Proc. Natl. Acad. Sci. USA*, 87:2264-2268 (1990).
Kohler and Milstein, "Continuous cultures of fused cells secreting antibody of predefined specificity", *Nature*, 256:495-497 (1975).
Lockhart, et al., "Expression monitoring by hybridization to high-density oligonucleotide arrays", *Nat. Biotechnol.*, 14:1675-1680 (1996).
McGall, et al., "Light-directed synthesis of high-density oligonucleotide arrays using semiconductor photoresists", *Proc. Nat. Acad. Sci. USA*, 93:13555-13460 (1996).
Ward, et al., "Binding activities of a repertoire of single immunoglobulin variable domains secreted from *Escherichia coli*", *Nature*, 341:544-546 (1989).
Barnes, et al., "Gene expression in juvenile arthritis and spondyloarthropathy: pro-angiogenic ELR+ chemokine genes relate to course of arthritis", *Rheumatology*, 43(8):973-9 (2004).
Deirmengian, et al., "The Mark Coventry Award: white blood cell gene expression: a new approach toward the study and diagnosis of infection", *Clin Orthop Relat Res.*, 440:38-44 (2005).
Friese, et al., "Release of endogenous anti-inflammatory complement regulators FHL-1 and factor H protects synovial fibroblasts during rheumatoid arthritis", *Clin Exp Immunol.*, 132(3):485-95 (2003).
Heller, et al., "Discovery and analysis of inflammatory disease-related genes using cDNA microarrays", *Proc Natl Acad Sci U S A.*, 94(6):2150-5 (1997).
O'Hara, et al., "Local expression of the serum amyloid A and formyl peptide receptor-like 1 genes in synovial tissue is associated with matrix metalloproteinase production in patients with inflammatory arthritis", *Arthritis Rheum.*, 50(6):1788-99 (2004).

(Continued)

*Primary Examiner*—Nancy Vogel
*Assistant Examiner*—Michele K. Joike
(74) *Attorney, Agent, or Firm*—Pabst Patent Group LLP

(57) ABSTRACT

A method of diagnosing the source of local, acute inflammation has been developed based on the discovery that white cells have different patterns of gene expression, and therefore protein markers, depending on the origin of the inflammation. These differences can be readily accessed by analysis of the white cells obtained at a site to be analyzed, for example, in the synovial fluid of a knee. The analysis, by comparison with the analysis of white cells present in known conditions, can be used to differentiate between inflammation due to bacterial infection, arthritis or gout, for example. The examples demonstrate differential gene expression in cells present in synovial fluid biopsies from patients with confirmed bacterial infection as compared to patients with aseptic loosening or patients with inflammation due to gout.

15 Claims, No Drawings

OTHER PUBLICATIONS

Pufe, et al., "Expression of pleiotrophin, an embryonic growth and differentiation factor, in rheumatoid arthritis", *Arthritis Rheum.*, 48(3):660-7 (2003).

Stuhlmuller, et al., "Identification of known and novel genes in activated monocytes from patients with rheumatoid arthritis", *Arthritis Rheum.*, 43(4):775-90 (2000).

Yerramilli, et al., "RNA expression patterns change dramatically in human neutrophils exposed to bacteria" Blood, 97(8):2457-68 (2001).

Zanders, et al., "Analysis of immune system gene expression in small rheumatoid arthritis biopsies using a combination of subtractive hybridization and high-density cDNA arrays" *J Immunol Methods.*, 233(1-2):131-40 (2000).

* cited by examiner

DIAGNOSTIC ASSAY FOR SOURCE OF INFLAMMATION

This claims priority under 35 U.S.C. 119 to U.S. Ser. No. 60/603,313 filed Aug. 20, 2004.

BACKGROUND OF THE INVENTION

The present invention is generally in the field of diagnostics for different types of inflammation, for example, whether the inflammation is due to bacterial infection or autoimmune disease.

The immune system is a bodywide network of cells and organs that has evolved to defend the body against attacks by "foreign" invaders. The proper targets of the immune system are infectious organisms—bacteria such as streptococci; Fungi; Parasites, including the microbes that cause schistosomiasis; and viruses such as herpes virus. The lymphoid organs are concerned with the growth, development, and deployment of lymphocytes, which are white blood cells that are key operatives of the immune system. The organs of the immune system are connected with one another and with other organs of the body by a network of lymphatic vessels similar to blood vessels. Immune cells and foreign particles are conveyed through the lymphatic vessels in lymph, a clear fluid that bathes the body's tissues. Cells destined to become immune cells, like all blood cells, arise in the bone marrow from so-called stem cells. Some develop into myeloid cells, a group typified by the large, cell- and particle-devouring white blood cells known as phagocytes; phagocytes include monocytes, macrophages, and neutrophils. Other myeloid descendants become granule-containing inflammatory cells such as eosinophils and basophils. Lymphoid precursors develop into the small white blood cells called lymphocytes. The two major classes of lymphocytes are B cells and T cells. B cells make antibodies. At least two types of lymphocytes are killer cells—cytotoxic T cells and natural killer cells. To attack, cytotoxic T cells need to recognize a specific antigen, whereas natural killer or NK cells do not. Both types contain granules filled with potent chemicals, and both types kill on contact. The killer binds to its target, aims its weapons, and delivers a burst of lethal chemicals. Phagocytes are large white cells that can engulf and digest foreign invaders. They include monocytes, which circulate in the blood, and macrophages, which are found in tissues throughout the body, as well as neutrophils, cells that circulate in the blood but move into tissues where they are needed. Macrophages are versatile cells; they act as scavengers, they secrete a wide variety of powerful chemicals, and they play an essential role in activating T cells. Neutrophils are not only phagocytes but also granulocytes: they contain granules filled with potent chemicals. These chemicals, in addition to destroying microorganisms, play a key role in acute inflammatory reactions. Other types of granulocytes are eosinophils and basophils. Mast cells are granule-containing cells in tissue.

When the immune system malfunctions, it can unleash a torrent of disorders and diseases. One of the most familiar is allergy. Allergies such as hay fever and hives are related to the antibody known as IgE. Sometimes the immune system's recognition apparatus breaks down, and the body begins to manufacture antibodies and T cells directed against the body's own cells and organs. Such cells and autoantibodies, as they are known, contribute to many diseases. For instance, T cells that attack pancreas cells contribute to diabetes, while an autoantibody known as rheumatoid factor is common in persons with rheumatoid arthritis.

Other types of inflammation may arise due to infection or damage to tissue due to trauma or excessive wear. Since treatments differ based on the origin of the disease or disorder, it is important to know what is eliciting the inflammation.

It is therefore an object of the present invention to provide a method and materials for rapid diagnosis of the source of inflammation.

SUMMARY OF THE INVENTION

A method of diagnosing the source of local, acute inflammation has been developed based on the discovery that white cells have different patterns of gene expression, and therefore different protein markers, depending on the origin of the inflammation. These differences can be readily accessed by analysis of the white cells obtained at a site to be analyzed, for example, in the synovial fluid of a knee. The analysis, by comparison with the analysis of white cells present in known conditions, can be used to differentiate between inflammation due to bacterial infection, arthritis or gout, for example. The method can also be used in drug screening, where changes in the expression patterns of known diseases or disorders to appear more normal in response to a particular treatment or drug is indicative of potential efficacy.

The examples demonstrate differential gene expression in cells present in synovial fluid biopsies from patients with confirmed bacterial infection as compared to patients with aseptic loosening or patients with inflammation due to gout.

DETAILED DESCRIPTION OF THE INVENTION

One of the hallmarks of inflammation is an influx of white blood cells into the injured area. For example, acute inflammation in knee infections, rheumatoid arthritis, Lyme disease, and gout all involve the participation of white blood cells. Since the acute cellular infiltrate has been historically considered to be a stereotyped response, there has been little attention given to studying these cells for diagnostic purposes. A few in vitro studies have suggested that monocytes, dendritic cells, and neutrophils have the ability to alter their gene expression depending on the source of inflammation. Using this information, it was postulated that the cells in an inflamed knee, despite appearing the same in different forms of inflammation, may have different and diagnostic gene expression profiles. This was demonstrated in the following examples comparing results in cells present in synovial fluid biopsies from patients with confirmed bacterial infection as compared to patients with aseptic loosening or patients with inflammation due to gout.

I. Samples to be Analyzed

Samples can be obtained for testing using standard techniques. Typically samples are obtained by biopsy or aspiration, for example, of tissue at a site to be analyzed, or of synovial joint fluid. Fluids commonly aspirated for the evaluation of acute inflammation include synovial fluid, sputum, urine, cerebrospinal fluid, peritoneal lavage fluid, pleural effusion, pericardial effusion, and abscesses among others. Tissues commonly biopsied for the analysis of acute inflammation include connective tissues such as bone, muscle, and synovium, solid organs such as liver, heart, kidney, and brain, and reactive tissues such as periprosthetic tissues.

Nucleic acid samples used in the methods and assays may be prepared by any available method or process. Methods of isolating total mRNA are also well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I Theory and Nucleic Acid Preparation, Tijssen, (1993) (editor) Elsevier Press. Such samples include RNA samples, cDNA synthesized from an mRNA sample isolated from a cell or tissue of interest, DNA amplified from the cDNA, and RNA transcribed from the amplified DNA. One of skill in the art would appreciate that it may be desirable to inhibit or destroy RNase present in homogenates before homogenates are analyzed.

As described in example 1, a method was developed to stabilize, isolate, and purify RNA from inflamed synovial fluid, as described in the following examples.

Biological samples may be of any biological tissue or fluid containing leukocytes. Frequently the sample will be a "clinical sample" which is a sample derived from a patient. Typical clinical samples include, but are not limited to, synovial fluid, sputum, blood, blood-cells (e.g., white cells), tissue or fine needle biopsy samples, urine, peritoneal fluid, cerebrospinal fluid, abscesses, and pleural fluid, or cells therefrom. Biological samples may also include sections of tissues, such as frozen sections or formalin fixed sections taken for histological purposes. Peroprosthetic tissues are often analyzed for evidence of infection.

Controls may either be normal (i.e., not infected or not-inflammed tissue, for example) or samples from known types or stages of infection or inflammation or other disease. As described below, comparison of the expression patterns of the sample to be tested with those of the controls can be used to diagnose the disease.

II. Methods of Analysis

Analysis for the purpose of monitoring differential gene expression may be focused on a variety of tissues and fluids, and may also be used to detect or measure a number of different molecular targets. When a cell expresses a gene, it transcribes the appropriate RNA, which is ultimately translated into a protein. The relevant protein may then be localized to a variety of intracellular or extracellular locations.

Methods of detecting or measuring gene expression may utilize methods that focus on cellular components (cellular examination), or methods that focus on examining extracellular components (fluid examination). Because gene expression involves the ordered production of a number of different molecules, a cellular or fluid examination may be used to detect or measure a variety of molecules including RNA, protein, and a number of molecules that may be modified as a result of the protein's function. Typical diagnostic methods focusing on nucleic acids include amplification techniques such as PCR and RT-PCR (including quantitative variants), and hybridization techniques such as in situ hybridization, microarrays, blots, and others. Typical diagnostic methods focusing on proteins include binding techniques such as ELISA, imunohistochemistry, microarray and functional techniques such as enzymatic assays.

Many biological functions are accomplished by altering the expression of various genes through transcriptional (e.g., through control of initiation, provision of RNA precursors, RNA processing, etc.) and/or translational control. For example, fundamental biological processes such as cell cycle, cell differentiation and cell death, are often characterized by variations in the expression levels of groups of genes. Changes in gene expression are also associated with pathogenesis. Thus, changes in the expression levels of particular genes serve as signposts for the presence and progression of various diseases or inflammation. As described herein, it is the differences in expression that are used to determine the origin of the inflammation—whether it is infection or aseptic inflammation, and if infection, whether it is viral, bacterial, or parasitic in origin. If the source is aseptic inflammation, one could determine the specific underlying disease process, as many autoimmune diseases that are associated with local inflammation. This is particularly important in certain clinical scenarios when pathogen detection is difficult and gross cellular examination is uninformative. The testing of expression of genes in the leukocytes at the site is much easier.

Monitoring changes in gene expression may also provide certain advantages during drug screening development. By determining what patterns of expression are associated with infection as compared to inflammation, one can then test for the effect of a drug, and whether treatment with a drug, or a particular dosage or treatment schedule is effective in normalizing the expression pattern.

Monitoring changes in gene expression may also provide information regarding a patient's susceptibility to disease and probability of recovering. This is especially important when treating patients with local infections and/or autoimmune diseases.

Definitions

In the description that follows, numerous terms and phrases known to those skilled in the art are used. In the interest of clarity and consistency of interpretation, the definitions of certain terms and phrases are provided.

As used herein, the phrase "detecting the level of expression" includes methods that quantify expression levels as well as methods that determine whether a gene of interest is expressed at all. Thus, an assay which provides a yes or no result without necessarily providing quantification of an amount of expression is an assay that requires "detecting the level of expression" as that phrase is used herein. As used herein, it is the pattern of expression in addition to the individual expression that is quantitated or qualified for analysis.

As used herein, oligonucleotide sequences that are complementary to one or more of the genes described herein refers to oligonucleotides that are capable of hybridizing under stringent conditions to at least part of the nucleotide sequence of the genes. Such hybridizable oligonucleotides will typically exhibit at least about 75% sequence identity at the nucleotide level to the genes, preferably about 80% or 85% sequence identity or more preferably about 90% or 95% or more sequence identity to the genes.

"Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

The terms "background" or "background signal intensity" refer to hybridization signals resulting from non-specific binding, or other interactions, between the labeled target nucleic acids and components of the oligonucleotide array (e.g. the oligonucleotide probes, control probes, the array substrate, etc.). Background signals may also be produced by intrinsic fluorescence of the array components themselves. A single background signal can be calculated for the entire array, or a different background signal may be calculated for each target nucleic acid. In a preferred embodiment, background is calculated as the average hybridization signal intensity for the lowest 5% to 10% of the probes in the array, or, where a different background signal is calculated for each target gene, for the lowest 5% to 10% of the probes for each gene. One of skill in the art will appreciate that where the probes to a particular gene hybridize well and thus appear to be specifically binding to a target sequence, they should not be used in a background signal calculation. Alternatively, background may be calculated as the average hybridization signal intensity produced by hybridization to probes that are not complementary to any sequence found in the sample (e.g., probes directed to nucleic acids of the opposite sense or to genes not found in the sample such as bacterial genes where the sample is mammalian nucleic acids). Background can also be calculated as the average signal intensity produced by regions of the array that lack any probes at all.

The phrase "hybridizing specifically to" refers to the binding, duplexing or hybridizing of a molecule substantially to or only to a particular nucleotide sequence or sequences under stringent conditions when that sequence is present in a complex mixture (e.g., total cellular) DNA or RNA.

Assays and methods may utilize available formats to simultaneously screen at least about 100, 1000, 10,000 or about 1,000,000 or more different nucleic acid hybridizations.

The terms "mismatch control" or "mismatch probe" refer to a probe whose sequence is deliberately selected not to be perfectly complementary to a particular target sequence. For each mismatch (MM) control in a high-density array there typically exists a corresponding perfect match (PM) probe that is perfectly complementary to the same particular target sequence. The mismatch may comprise one or more bases. While the mismatch(s) may be located anywhere in the mismatch probe, terminal mismatches are less desirable as a terminal mismatch is less likely to prevent hybridization of the target sequence. In a particularly preferred embodiment, the mismatch is located at or near the center of the probe such that the mismatch is most likely to destabilize the duplex with the target sequence under the test hybridization conditions.

The term "perfect match probe" refers to a probe that has a sequence that is perfectly complementary to a particular target sequence. The test probe is typically perfectly complementary to a portion (subsequence) of the target sequence. The perfect match (PM) probe can be a "test probe", a "normalization control" probe, an expression level control probe and the like. A perfect match control or perfect match probe is, however, distinguished from a "mismatch control" or "mismatch probe."

As used herein a "probe" is defined as a nucleic acid, preferably an oligonucleotide, capable of binding to a target nucleic acid of complementary sequence through one or more types of chemical bonds, usually through complementary base pairing, usually through hydrogen bond formation. As used herein, a probe may include natural (i.e., A, G, U, C or T) or modified bases (7-deazaguanosine, inosine, etc.). In addition, the bases in probes may be joined by a linkage other than a phosphodiester bond, so long as it does not interfere with hybridization. Thus, probes may be peptide nucleic acids in which the constituent bases are joined by peptide bonds rather than phosphodiester linkages.

The term "stringent conditions" refers to conditions under which a probe will hybridize to its target subsequence, but with only insubstantial hybridization to other sequences or to other sequences such that the difference may be identified. Stringent conditions are sequence-dependent and will be different in different circumstances. Longer sequences hybridize specifically at higher temperatures. Generally, stringent conditions are selected to be about 5° C. lower than the thermal melting point ($T_m$) for the specific sequence at a defined ionic strength and pH.

Typically, stringent conditions will be those in which the salt concentration is at least about 0.01 to 1.0 M sodium ion concentration (or other salts) at pH 7.0 to 8.3 and the temperature is at least about 30° C. for short probes (e.g., 10 to 50 nucleotides). Stringent conditions may also be achieved with the addition of destabilizing agents such as formamide.

The "percentage of sequence identity" or "sequence identity" is determined by comparing two optimally aligned sequences or subsequences over a comparison window or span, wherein the portion of the polynucleotide sequence in the comparison window may optionally comprise additions or deletions (i.e., gaps) as compared to the reference sequence (which does not comprise additions or deletions) for optimal alignment of the two sequences. The percentage is calculated by determining the number of positions at which the identical subunit (e.g., nucleic acid base or amino acid residue) occurs in both sequences to yield the number of matched positions, dividing the number of matched positions by the total number of positions in the window of comparison and multiplying the result by 100 to yield the percentage of sequence identity. Percentage sequence identity when calculated using the programs GAP or BESTFIT is calculated using default gap weights.

Homology or identity may be determined by BLAST (Basic Local Alignment Search Tool) analysis using the algorithm employed by the programs blastp, blastn, blastx, tblastn and tblastx (Karlin et al., Proc. Natl. Acad. Sci. USA 87, 2264-2268 (1990) and Altschul, J. Mol. Evol. 36,290-300 (1993), fully incorporated by reference) which are tailored for sequence similarity searching. The approach used by the BLAST program is to first consider similar segments between a query sequence and a database sequence, then to evaluate the statistical significance of all matches that are identified and finally to summarize only those matches which satisfy a preselected threshold of significance. For a discussion of basic issues in similarity searching of sequence databases, see Altschul et al., Nature Genet. 6, 119-129 (1994). The search parameters for histogram, descriptions, alignments, expect (i.e., the statistical significance threshold for reporting matches against database sequences), cutoff, matrix and filter are at the default settings. The default scoring matrix used by blastp, blastx, tblasta, and tblastx is the BLOSUM62 matrix (Henikoff et al., Proc. Natl. Acad. Sci. USA 89, 10915-10919 (1992). Four blastn parameters were adjusted as follows Q=10 (gap creation penalty); R=10 (gap extension penalty); wink=1 (generates word hits at every winks position along the query); and gapw=16 (sets the window width within which gapped alignments are generated). The equivalent Blastp parameter settings were Q=9; R=2; wink=1; and gapw=32. A Bestfit comparison between sequences, available in the GCG package version 10.0, uses DNA parameters GAP=50 (gap creation penalty) and LENz=3 (gap extension penalty) and the equivalent settings in protein comparisons are GAP=8 and LEN=2.

For a particular interrogation of two conditions or sources, it is desirable to select those genes that display a great difference in the expression pattern between the two conditions or sources. At least a two-fold difference is desirable, but a three, five-fold or ten-fold difference may be preferred. Interrogations of the genes or proteins can be performed to yield information on gene expression as well as on the levels of the encoded proteins.

Comparison of the expression data, as well as available sequence or other information may be done by researcher or diagnostician or may be done with the aid of a computer and databases as described herein.

Assay Formats

The genes identified as being differentially expressed may be assessed in a variety of nucleic acid detection assays to detect or quantify the expression level of a gene or multiple genes in a given sample. For example, traditional Northern blotting, nuclease protection, RT-PCR, microarray, and differential display methods may be used for detecting gene expression levels. Methods for assaying for mRNA include Northern blots, slot blots, dot blots, and hybridization to an ordered array of oligonucleotides. Any method for specifically and quantitatively measuring a specific protein or mRNA or DNA product can be used. However, methods and assays are most efficiently designed with array or chip hybridization-based methods for detecting the expression of a large number of genes. Any hybridization assay format may be used, including solution-based and solid support-based assay formats.

The protein products of the genes identified herein can also be assayed to determine the amount of expression. Methods for assaying for a protein include Western blot, immunoprecipitation, and radioimmunoassay. The proteins analyzed may be localized intracellularly (most commonly an application of immunohistochemistry) or extracellularly (most commonly an application of immunoassays such as ELISA).

In another format, the relative amounts of proteins produced in a cell population may be analyzed for purposes of diagnosis or the protein from cellular population that has been exposed to an agent to be tested may be compared to the amount produced in an unexposed control cell population. In this format, probes such as specific antibodies are used to monitor the differential expression of the protein in the different cell populations. Cell lines or populations are exposed to the agent to be tested under appropriate conditions and time. Cellular lysates may be prepared from the exposed cell line or population and a control, unexposed cell line or population. The cellular lysates are then analyzed with the probe, such as a specific antibody.

As noted above, the genes may be assayed in any convenient form. For example, they may be assayed in the form mRNA or reverse transcribed mRNA. The genes may be cloned or not and the genes may be amplified or not. The cloning itself does not appear to bias the representation of genes within a population. However, it may be preferable to use polyA+ RNA as a source, as it can be used with less processing steps. In some embodiments, it may be preferable to assay the protein or peptide encoded by the gene.

The sequences of many of the expression marker genes are in the public databases such as GenBank. The sequences of the genes in GenBank are publicly available at, for example, www.ncbi.nih.gov. IMAGE gives the clone number from the IMAGE consortium. Information on the genes in the Affymetrix® arrays can also be obtained from Affymetrix®.

One of skill in the art will appreciate that an enormous number of array designs are suitable. The high density array will typically include a number of probes that specifically hybridize to the sequences of interest. See WO 99/32660 for methods of producing probes for a given gene or genes. In a preferred embodiment, the array will include one or more control probes.

High density array chips include "test probes." Test probes may be oligonucleotides that range from about 5 to about 500 or about 5 to about 50 nucleotides, more preferably from about 10 to about 40 nucleotides and most preferably from about 15 to about 40 nucleotides in length. In other particularly preferred embodiments, the probes are about 20 or 25 nucleotides in length. In another preferred embodiment, test probes are double or single strand DNA sequences. DNA sequences may be isolated or cloned from natural sources or amplified from natural sources using natural nucleic acid as templates. These probes have sequences complementary to particular subsequences of the genes whose expression they are designed to detect. Thus, the test probes are capable of specifically hybridizing to the target nucleic acid they are to detect.

In addition to test probes that bind the target nucleic acid(s) of interest, the high density array can contain a number of control probes. The control probes fall into three categories referred to herein as normalization controls; expression level controls; and mismatch controls. Normalization controls are oligonucleotide or other nucleic acid probes that are complementary to labeled reference oligonucleotides or other nucleic acid sequences that are added to the nucleic acid sample. The signals obtained from the normalization controls after hybridization provide a control for variations in hybridization conditions, label intensity, "reading" efficiency and other factors that may cause the signal of a perfect hybridization to vary between arrays. In a preferred embodiment, signals (e.g. fluorescence intensity) read from all other probes in the array are divided by the signal (, fluorescence intensity) from the control probes thereby normalizing the measurements. Virtually any probe may serve as a normalization control. However, it is recognized that hybridization efficiency varies with base composition and probe length. Preferred normalization probes are selected to reflect the average length of the other probes present in the array; however, they can be selected to cover a range of lengths. The normalization control(s) can also be selected to reflect the (average) base composition of the other probes in the array, however in a preferred embodiment, only one or a few probes are used and they are selected such that they hybridize well (i.e., no secondary structure) and do not match any target-specific probes. Expression level controls are probes that hybridize specifically with constitutively expressed genes in the biological sample. Virtually any constitutively expressed gene provides a suitable target for expression level controls. Typical expression level control probes have sequences complementary to subsequences of constitutively expressed "housekeeping genes" including the .beta.-actin gene, the transferrin receptor gene, and the GAPDH gene. Mismatch controls may also be provided for the probes to the target genes, for expression level controls or for normalization controls. Mismatch controls are oligonucleotide probes or other nucleic acid probes identical to their corresponding test or control probes except for the presence of one or more mismatched bases. A mismatched base is a base selected so that it is not complementary to the corresponding base in the target sequence to which the probe would otherwise specifically hybridize. One or more mismatches are selected such that under appropriate hybridization conditions (e.g., stringent conditions) the test or control probe would be expected to hybridize with its target sequence, but the mismatch probe would not hybridize (or would hybridize to a significantly lesser extent). Preferred mismatch probes contain a central mismatch. Thus, for example, where a probe is a twenty-mer, a corresponding mismatch probe may have the identical sequence except for a single base mismatch (e.g., substituting a G, a C or a T for an A) at any of positions 6 through 14 (the central mismatch). Mismatch probes thus provide a control for non-specific binding or cross hybridization to a nucleic acid in the sample other than the target to which the probe is directed. Mismatch probes also indicate whether hybridization is specific or not.

Solid Supports

Solid supports containing oligonucleotide probes for differentially expressed genes can be any solid or semisolid support material known to those skilled in the art. Suitable examples include, but are not limited to, membranes, filters, tissue culture dishes, polyvinyl chloride dishes, beads, test strips, silicon or glass based chips and the like. Suitable glass wafers and hybridization methods are widely available. Any solid surface to which oligonucleotides can be bound, either directly or indirectly, either covalently or non-covalently, can be used. In some embodiments, it may be desirable to attach some oligonucleotides covalently and others non-covalently to the same solid support. A preferred solid support is a high density array or DNA chip. These contain a particular oligonucleotide probe in a predetermined location on the array. Each predetermined location may contain more than one molecule of the probe, but each molecule within the predetermined location has an identical sequence. Such predetermined locations are termed features. There may be, for example, from 2, 10, 100, 1000 to 10,000, 100,000 or 400,000 of such features on a single solid support. The solid support or the area within which the probes are attached may be on the order of a square centimeter. Methods of forming high density arrays of oligonucleotides with a minimal number of synthetic steps are known. The oligonucleotide analogue array can be synthesized on a solid substrate by a variety of methods, including, but not limited to, light-directed chemical coupling, and mechanically directed coupling (see U.S. Pat. No. 5,143,854 to Pirrung et al.; U.S. Pat. No. 5,800,992 to Fodor et al.; U.S. Pat. No. 5,837,832 to Chee et al.

In brief, the light-directed combinatorial synthesis of oligonucleotide arrays on a glass surface proceeds using automated phosphoramidite chemistry and chip masking techniques. In one specific implementation, a glass surface is derivatized with a silane reagent containing a functional group, e.g., a hydroxyl or amine group blocked by a photolabile protecting group. Photolysis through a photolithographic mask is used selectively to expose functional groups which are then ready to react with incoming 5' photoprotected nucleoside phosphoramidites. The phosphoramidites react only with those sites which are illuminated (and thus exposed by removal of the photolabile blocking group). Thus, the phosphoramidites only add to those areas selectively exposed from the preceding step. These steps are repeated until the desired array of sequences has been synthesized on the solid surface. Combinatorial synthesis of different oligonucleotide analogues at different locations on the array is determined by the pattern of illumination during synthesis and the order of addition of coupling reagents.

In addition to the foregoing, methods which can be used to generate an array of oligonucleotides on a single substrate are described in WO 93/09668 to Fodor et al. High density nucleic acid arrays can also be fabricated by depositing premade or natural nucleic acids in predetermined positions. Synthesized or natural nucleic acids are deposited on specific locations of a substrate by light directed targeting and oligonucleotide directed targeting. Another embodiment uses a dispenser that moves from region to region to deposit nucleic acids in specific spots.

Oligonucleotide probe arrays for expression monitoring can be made and used according to any techniques known in the art (see for example, Lockhart et al., Nat. Biotechnol. 14, 1675-1680 (1996); McGall et al., Proc. Nat. Acad. Sci. USA 93, 13555-13460 (1996). Such probe arrays may contain at least two or more oligonucleotides that are complementary to or hybridize to two or more of the genes described herein. Such arrays may also contain oligonucleotides that are complementary to or hybridize to at least 3, 4, 5, 6, 7, 8, 9, 10, 20, 30, 50, 70 or more of the genes described therein.

Gene Signature Differential analysis.

Gene Signature Differential analysis is a method designed to detect genes present in one sample set, and absent in another. Genes with differential expression in cells from sites of infection or inflammation versus normal tissue are better diagnostic and therapeutic targets than genes that do not change in expression.

Hybridization

Nucleic acid hybridization simply involves contacting a probe and target nucleic acid under conditions where the probe and its complementary target can form stable hybrid duplexes through complementary base pairing (see WO 99/32660 to Lockhart). The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA-DNA, RNA-RNA or RNA-DNA) will form even where the annealed sequences are not perfectly complementary. Thus, specificity of hybridization is reduced at lower stringency. Conversely, at higher stringency (e.g., higher temperature or lower salt) successful hybridization requires fewer mismatches. One of skill in the art will appreciate that hybridization conditions may be selected to provide any degree of stringency. In a preferred embodiment, hybridization is performed at low stringency, in this case in 6×SSPE-T at 37° C. (0.005% Triton x-100) to ensure hybridization and then subsequent washes are performed at higher stringency (e.g., 1×SSPE-T at 37° C.) to eliminate mismatched hybrid duplexes. Successive washes may be performed at increasingly higher stringency (e.g. down to as low as 0.25×SSPE-T at 37° C. to 50° C. until a desired level of hybridization specificity is obtained. Stringency can also be increased by addition of agents such as formamide. Hybridization specificity may be evaluated by comparison of hybridization to the test probes with hybridization to the various controls that can be present (e.g., expression level controls, normalization controls, mismatch controls, etc.).

In general, there is a tradeoff between hybridization specificity (stringency) and signal intensity. Thus, in a preferred embodiment, the wash is performed at the highest stringency that produces consistent results and that provides a signal intensity greater than approximately 10% of the background intensity. The hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest.

Signal Detection

The hybridized nucleic acids are typically detected by detecting one or more labels attached to the sample nucleic acids. The labels may be incorporated by any of a number of means well known to those of skill in the art (see WO 99/32660 to Lockhart). Any suitable methods can be used to detect one or more of the markers described herein. For example, gas phase ion spectrometry can be used. This technique includes, e.g., laser desorption/ionization mass spectrometry. In some embodiments, the sample can be prepared prior to gas phase ion spectrometry, e.g., pre-fractionation, two-dimensional gel chromatography, high performance liquid chromatography, etc. to assist detection of markers. Detection of markers can be achieved using methods other than gas phase ion spectrometry. For example, traditional immunoassays (e.g., ELISA) can be used to detect the markers in a sample. These detection methods are described in detail below.

Detection by Gas Phase Ion Spectrometry

Markers present in a sample can also be detected using gas phase ion spectrometry, and more preferably, using mass spectrometry. In one embodiment, matrix-assisted laser desorption/ionization ("MALDI") mass spectrometry can be used. In MALDI, the sample is typically quasi-purified to obtain a fraction that essentially consists of a marker or markers using protein separation methods such as two-dimensional gel electrophoresis or high performance liquid chromatography (HPLC).

In another embodiment, surface-enhanced laser desorption/ionization mass spectrometry ("SELDI") can be used. SELDI uses a substrate comprising adsorbents to capture markers, which can then be directly desorbed and ionized from the substrate surface during mass spectrometry. Since the substrate surface in SELDI captures markers, a sample need not be quasi-purified as in MALDI. However, depending on the complexity of a sample and the type of adsorbents used, it may be desirable to prepare a sample to reduce its complexity prior to SELDI analysis.

Various sample preparation methods to assist detection of markers in a sample and gas phase ion spectrometry methods are described in detail below. Optionally, one or combination of methods described below or other methods known in the art can be used to prepare a sample to further assist detection and characterization of markers in a sample. In some embodiments, a sample can be pre-fractionated to provide a less complex sample prior to gas phase ion spectrometry analysis. Moreover, pre-fractionation protocols can provide additional information regarding physical and chemical characteristics of markers. For example, if a sample was pre-fractionated using an anion-exchange spin column, and if a marker is eluted at a certain pH, this elution characteristic provides information regarding binding properties of the marker. In another example, a sample can be pre-fractionated by removing proteins or other molecules in the sample that are present in a high quantity or that may interfere with the detection of markers in a sample. In another embodiment, a sample can be pre-fractionated according to size of proteins in a sample using size exclusion chromatography. For a biological sample wherein the amount of sample available is small, preferably a size selection spin column is used. For example, K-30 spin column (Ciphergen Biosystems, Inc.) can be used. In general, the first fraction that is eluted from the column ("fraction 1") has the highest percentage of high molecular weight proteins; fraction 2 has a lower percentage of high molecular weight proteins; fraction 3 has even a lower percentage of high molecular weight proteins; fraction 4 has the lowest amount of large proteins; and so on. Each fraction can then be analyzed by gas phase ion spectrometry for the detection of markers. In still another embodiment, biomolecules in a sample can be separated by high-resolution electrophoresis, e.g., one or two-dimensional gel electrophoresis. A fraction containing a marker can be isolated and further analyzed by gas phase ion spectrometry. Preferably, two-dimensional gel electrophoresis is used to generate two-dimensional array of spots of biomolecules, including one or more markers. See, e.g., Jungblut and Thiede, Mass Spectr. Rev. 16:145-162 (1997).

The two-dimensional gel electrophoresis can be performed using methods known in the art. See, e.g., Deutscher ed., Methods In Enzymology vol. 182. Typically, biomolecules in a sample are separated by, e.g., isoelectric focusing, during which biomolecules in a sample are separated in a pH gradient until they reach a spot where their net charge is zero (i.e., isoelectric point). This first separation step results in one-dimensional array of biomolecules. The biomolecules in one dimensional array is further separated using a technique generally distinct from that used in the first separation step. For example, in the second dimension, biomolecules separated by isoelectric focusing are further separated using a polyacrylamide gel, such as polyacrylamide gel electrophoresis in the presence of sodium dodecyl sulfate (SDS-PAGE). SDS-PAGE gel allows further separation based on molecular mass of biomolecules. Typically, two-dimensional gel electrophoresis can separate chemically different biomolecules in the molecular mass range from 1000-200,000 Da within complex mixtures.

Biomolecules in the two-dimensional array can be detected using any suitable methods known in the art. For example, biomolecules in a gel can be labeled or stained (e.g. Coomassie Blue or silver staining). If gel electrophoresis generates spots that correspond to the molecular weight of one or more markers of the invention, the spot can be is further analyzed by gas phase ion spectrometry. For example, spots can be excised from the gel and analyzed by gas phase ion spectrometry. Alternatively, the gel containing biomolecules can be transferred to an inert membrane by applying an electric field. Then a spot on the membrane that approximately corresponds to the molecular weight of a marker can be analyzed by gas phase ion spectrometry. In gas phase ion spectrometry, the spots can be analyzed using any suitable techniques, such as MALDI or SELDI (e.g., using ProteinChip.RTM. array) as described in detail below.

Prior to gas phase ion spectrometry analysis, it may be desirable to cleave biomolecules in the spot into smaller fragments using cleaving reagents, such as proteases (e.g., trypin). The digestion of biomolecules into small fragments provides a mass fingerprint of the biomolecules in the spot, which can be used to determine the identity of markers if desired.

High Performance Liquid Chromatography

In yet another embodiment, high performance liquid chromatography (HPLC) can be used to separate a mixture of biomolecules in a sample based on their different physical properties, such as polarity, charge and size. HPLC instruments typically consist of a reservoir of mobile phase, a pump, an injector, a separation column, and a detector. Biomolecules in a sample are separated by injecting an aliquot of the sample onto the column. Different biomolecules in the mixture pass through the column at different rates due to differences in their partitioning behavior between the mobile liquid phase and the stationary phase. A fraction that corresponds to the molecular weight and/or physical properties of one or more markers can be collected. The fraction can then be analyzed by gas phase ion spectrometry to detect markers. For example, the spots can be analyzed using either MALDI or SELDI (e.g., using ProteinChip.RTM. array).

Desorption/Ionization and Detection

Markers can be ionized using gas phase ion spectrometry. Any suitable gas phase ion spectrometers can be used as long as it allows markers on the substrate to be resolved. Preferably, gas phase ion spectrometers allow quantitation of markers. In one embodiment, a gas phase ion spectrometer is a mass spectrometer. In a typical mass spectrometer, a substrate or a probe comprising markers on its surface is introduced into an inlet system of the mass spectrometer. The markers are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a detector. The detector then translates information of the detected ions into mass-to-charge ratios. Detection of the presence of markers or other substances will typically involve detection of signal intensity. This, in turn, can reflect the quantity and character of markers bound to the substrate. In laser desorption mass spectrometry, a substrate or a probe comprising markers is introduced into an inlet system. The markers are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of markers of specific mass to charge ratio. In another embodiment, an ion mobility spectrometer can be used to detect markers. The principle of ion mobility spectrometry is based on different mobility of ions. Specifically, ions of a sample produced by ionization move at different rates, due to their difference in, e.g., mass, charge, or shape, through a tube under the influence of an electric field. The ions (typically in the form of a current) are registered at the detector which can then be used to identify a marker or other substances in a sample. One advantage of ion mobility spectrometry is that it can operate at atmospheric pressure. In yet another embodiment, a total ion current measuring device can be used to detect and characterize markers. This device can be used when the substrate has only a single type of marker. When a single type of marker is on the substrate, the total current generated from the ionized marker reflects the quantity and other characteristics of the marker. The total ion current produced by the marker can then be compared to a control (e.g., a total ion current of a known compound). The quantity or other characteristics of the marker can then be determined.

Detection by Immunoassay

In another embodiment, an immunoassay can be used to detect and analyze markers in a sample. This method comprises: (a) providing an antibody that specifically binds to a marker; (b) contacting a sample with the antibody; and (c) detecting the presence of a complex of the antibody bound to the marker in the sample. To prepare an antibody that specifically binds to a marker, purified markers or their nucleic acid sequences can be used. Nucleic acid and amino acid sequences for markers can be obtained by further characterization of these markers. Using the purified markers or their nucleic acid sequences, antibodies that specifically bind to a marker can be prepared using any suitable methods known in the art. See, e.g., Coligan, Current Protocols in Immunology (1991); Harlow & Lane, Antibodies: A Laboratory Manual (1988); Goding, Monoclonal Antibodies: Principles and Practice (2d ed. 1986); and Kohler & Milstein, Nature 256: 495-497 (1975). Such techniques include, but are not limited to, antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341: 544-546 (1989)).

After the antibody is provided, a marker can be detected and/or quantified using any of suitable immunological binding assays known in the art (see, e.g., U.S. Pat. Nos. 4,366, 241; 4,376,110; 4,517,288; and 4,837,168). Useful assays include, for example, an enzyme immune assay (EIA) such as enzyme-linked immunosorbent assay (ELISA), a radioimmune assay (RIA), a Western blot assay, or a slot blot assay. These methods are also described in, e.g., Methods in Cell Biology: Antibodies in Cell Biology, volume 37 (Asai, ed. 1993); Basic and Clinical Immunology (Stites & Terr, eds., 7th ed. 1991); and Harlow & Lane, supra.

Generally, a sample obtained from a subject can be contacted with the antibody that specifically binds the marker. Optionally, the antibody can be fixed to a solid support to facilitate washing and subsequent isolation of the complex, prior to contacting the antibody with a sample. Examples of solid supports include glass or plastic in the form of, e.g., a microtiter plate, a stick, a bead, or a microbead. Antibodies can also be attached to a probe substrate or ProteinChip.RTM. array and can be analyzed by gas phase ion spectrometry as described above. The sample is preferably a biological fluid sample taken from a subject. Examples of biological samples include urine, barbotage, blood, serum, plasma, tears, saliva, cerebrospinal fluid, urine, tissue, etc. In a preferred embodiment, the biological fluid comprises synovial fluid. The sample can be diluted with a suitable diluent before contacting the sample to the antibody.

After incubating the sample with antibodies, the mixture is washed and the antibody-marker complex formed can be detected. This can be accomplished by incubating the washed mixture with a detection reagent. This detection reagent may be, e.g., a second antibody which is labeled with a detectable label. Exemplary detectable labels include magnetic beads (e.g., DYNABEADS.TM.), fluorescent dyes, radiolabels, enzymes (e.g., horse radish peroxide, alkaline phosphatase and others commonly used in an ELISA), and calorimetric labels such as colloidal gold or colored glass or plastic beads. Alternatively, the marker in the sample can be detected using an indirect assay, wherein, for example, a second, labeled antibody is used to detect bound marker-specific antibody, and/or in a competition or inhibition assay wherein, for example, a monoclonal antibody which binds to a distinct epitope of the marker is incubated simultaneously with the mixture.

Databases

Databases may contain information associated with a given cell or tissue sample such as descriptive information concerning the clinical status of the tissue sample, or the patient from which the sample was derived. The database may be designed to include different parts, for instance a sequences database and a gene expression database. Methods for the configuration and construction of such databases are widely available, for instance, see U.S. Pat. No. 5,953,727 Akerblom et al. Any appropriate computer platform may be used to perform the necessary comparisons between sequence information, gene expression information and any other information in the database or provided as an input. For example, a large number of computer workstations are available from a variety of manufacturers, such has those available from Silicon Graphics. Client-server environments, database servers and networks are also widely available and appropriate platforms for the databases of the invention. The databases may be used to produce, among other things, electronic Northerns to allow the user to determine the cell type or tissue in which a given gene is expressed and to allow determination of the abundance or expression level of a given gene in a particular tissue or cell.

Patterns can be compared manually (by a person) or by a computer or other machine. An algorithm can be used to detect similarities and differences. The algorithm may score and compare, for example, the genes which are expressed and the genes which are not expressed. Alternatively, the algorithm may look for changes in intensity of expression of a particular gene and score changes in intensity between two samples. A variety of such algorithms are known in the art. Similarities may be determined on the basis of genes which are expressed in both samples and genes which are not expressed in both samples or on the basis of genes whose intensity of expression are numerically similar. Differences are considered significant when they are greater than 2-fold, 3-fold or 5-fold from the base value. Alternatively, a mathematical approach can be used to conclude whether differences in the gene expression exhibited by different samples is significant (see, e.g., Golub et al., Science 286, 531 (1999). One approach to determine whether a sample is more similar to or has maximum similarity with a given condition (e.g., a particular grade or stage of tumor progression) is to compare the Euclidean distances (see Golub et al. and Example 6) between the sample and one or more pools representing different conditions for comparison; the pool with the smallest vector angle is then chosen as the most similar to the test sample among the pools compared.

Diagnostic Kits

Kits can be prepared for use within any of the above diagnostic methods. Such kits typically include two or more components necessary for performing a diagnostic assay Components may be compounds, reagents, containers and/or equipment. For example, one container within a kit may contain a monoclonal antibody or fragment thereof that specifically binds to protein found to be differentially expressed in a specific type of local inflammation. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a protein in a biological sample. Such kits generally comprise at least one oligonucleotide probe or primer, as described above, that hybridizes to a polynucleotide encoding a lung tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a protein.

In one example, a patient has an acutely inflamed total knee arthroplasty site. The knee effusion is aspirated and RNA is isolated and purified from the fluid's cellular content. The gene expression of cells in the fluid is determined using an Affymetrix® U133A Human microarray chip. The pattern of gene expression (all or one or more of those identified as described in the examples by comparison to known controls) is found to match the pattern exhibited by other cases of acute infection. Specific microarrays could be generated and included in a kit, allowing the specific evaluation of genes known to be differentially expressed in local inflammatory conditions. In another example, a patient has an acutely inflamed total knee arthroplasty site. The knee effusion is aspirated and the fluid is stored in a fashion that preserves overall protein integrity. The inflamed fluid is used as the sample for ELISA testing. The sample can be diluted before testing. ELISA testing is directed at detection of proteins that are products of genes found to be differentially expressed in various forms of local inflammation. The protein expression levels, measured by ELISA, are compared to sample standards in order to assign a diagnosis. A kit could be provided, utilizing immunochemistry in fluid or solid state, to measure the levels of a specific set of genes to aid in the diagnosis of local inflammatory diseases. In yet another example, a sample is attained through biopsy or surgical excision. It may be prepared in a variety of methods including frozen section, paraffin embedding, etc. Once on a slide, it is stained with antibody and marker preparations. An antibody to a gene that is upregulated in a specific form of inflammation is used to stain the sample. The white blood cells ("WBC") on the slide are then analyzed for evidence of gene expression based on protein binding. A single or combination of antibodies could be used on solid tissue, in an effort to diagnose the underlying etiology of inflammation. They could be provided together in a kit for the pathologic diagnosis of local acute inflammatory diseases and conditions.

The following examples are offered by way of illustration and not by way of limitation.

EXAMPLE 1

Method of RNA Isolation from Synovial Fluid Lymphocytes

Suitable RNA stabilizing solutions are commercially available, for example, from Ambion, Inc.
1. Synovial fluid is added to RNAlater® (Ambion Inc.) at a 1:3 ratio and is immediately mixed.
2. The mixture is stable at room temperature for 3 hours, in a clinical refrigerator for 1 day and in a freezer indefinitely.
3. Centrifuge 2 cc sample for 1 minute in a microfuge.
4. Remove the supernatant and add 800 µl lysis fluid (Ambion Inc.), and 50 µl of sodium acetate solution (Ambion Inc.)
5. Resuspend pellet with an 18 g needle and syringe.
6. Add 500 µl of Acid-phenol:chloroform and vortex 30 seconds.
7. Incubate at room temperature for 5 min. then microfuge for 10 min.
8. Transfer upper aqueous phase to a new tube.
9. Add ½ volume of 100% ethanol and mix.
10. Pass 9 through a filter cartridge (Ambion Inc.) and wash with 700 µl of wash solution 1 ((Ambion Inc.).
11. Wash 2× with 700 µl of wash solution 2/3 (Ambion Inc.)
12. Spin on microfuge for 1 minute to dry.
13. Elute with elution buffer (Ambion Inc.)

EXAMPLE 2

Isolating and Evaluating RNA from Inflammatory Fluids, for the Purposes of Identifying Differential Expression This example describes the identification of genes that are differentially expressed in the acute synovial fluid infiltrate that results after *S. aureus* joint infection. The acute synovial infiltrate resulting from gout is used as an aseptic control.

Synovial fluid samples were aspirated from seven patients with acute *S. aureus* knee infections and five patients with acute gout of the knee. Some patients had total knee arthroplasties. All patients in both groups had approximately 90% neutrophils in the synovial fluid. All patients with *S. aureus* infection exhibited fever, acute arthritis, multiple positive *S. aureus* cultures, high CRP values (average, 22; range, 1.9-34), high ESR (average, 90; range, 39-125), and an elevated synovial WBC count (average, 90,000 cells/mm$^3$; range, 27,000-183,000; average differential, 93% neutrophils). Five samples were from infected total knee arthroplasties and two samples were from infected native knees. All patient samples with gout revealed monosodium urate crystals, elevated synovial WBC count (average, 10,000; range, 800-16,000, average differential 90% neutrophils) and clinical resolution without antibiotics. All samples were in native knees.

The synovial fluid was added in a 1:3 ratio to RNAlater (Ambion Inc.) for stabilization and preservation of the RNA profile in the inflammatory cells of the fluid, as described in example 1. The mixture was agitated and stored at 20 degrees Celsius for eventual isolation and purification of RNA. At a later date, each sample mixture was centrifuged for collection of the inflammatory cells. The pellet was resuspended in a homogenization buffer and agitated by needle technique using a 10 cc syringe and an 18 gauge needle. Phenol:chloroform extraction techniques were used to create an aqueous layer of fluid containing partially purified RNA. The aqueous layer was then applied to an RNA binding filter (Ambion Inc.) attached to a microfuge tube. The bound RNA was washed with a variety of detergent buffers and finally eluted with hot elution buffer. The resulting fluid was assessed by spectrophotometry and the Agilent bioanalyzer for RNA purity and quantity. The RNA was found to be pure.

The RNA samples were then applied to Affymetrix® microarrays (U133A). All protocols were conducted as described in the Affymetrix® GeneChip Expression Analysis Technical Manual. Briefly, 5 µg of total RNA was converted to first-strand cDNA using Superscript II reverse transcriptase. Second-strand cDNA synthesis was followed by in vitro transcription for linear amplification of each transcript and incorporation of biotinylated CTP and UTP. The cRNA products were fragmented to 200 nucleotides or less, and hybridized for 16 hours to the microarrays. The microarrays were then washed at low (6×SSPE) and high (100 mM MES, 0.1M NaCl) stringency and stained with streptavidin-phycoerythrin. Fluorescence was amplified by adding biotinylated anti-streptavidin and an additional aliquot of streptavidin-phycoerythrin stain. A confocal scanner was used to collect fluorescence signal at 3 um resolution after excitation at 570 nm. The average signal from two sequential scans was calculated for each microarray feature. It was found that even though the two groups (gout and S. aureus) had similar cell and differential counts on synovial fluid analysis, the gene expression signatures in these cells was very different. Tables I and II list the gene expression in order of greatest change. About 1600 genes showed a statistically different expression level between the two groups, as shown in Table I (upregulation in septic versus aseptic inflammation) and Table II (downregulation in septic versus aseptic inflammation). As indicated in Tables I and II, "source" can be inputted into the internet (GeneBank) or through Affymetrix® to obtain the name, description and other identifying information relating to each gene and encoded product. The results are ordered by degree of change in expression.

This study established that one can analyze white blood cell or neutrophil gene expression as a diagnostic tool anywhere in the body or using a sample extracted from the body, for example, in synovial fluid. More specifically, it has been demonstrated in vivo, that an acute white blood cell infiltrate is associated with a gene expression profile that is specific for the underlying source of inflammation.

EXAMPLE 3

Identification of Genes that are Differentially Expressed between Patients with Acute Infection and Aseptic Loosening The materials and methods are identical to those described in Example 1 with the following exceptions.

Genes were identified that are differentially expressed in acute synovial fluid infiltrate between patients with acute infection and patients with aseptic loosening of total knee arthroplasty. Aseptic loosening is a loosening of the total joint without involvement of bacteria. Five patients with acute infection, which met strict inclusion criteria including purulence, high synovial white blood cell (WBC) count, high Erythrocyte sedimentation rate (ESR)/C-reactive protein (CRP) lab values, and positive microbial culture were analyzed. Eleven patients with aseptic loosening, which had low ESR/CRP lab values, low synovial WBC count, negative microbial cultures, and x-ray evidence of a loose arthroplasty were analyzed.

RNA was isolated from the cells in the synovial aspirate, and prepared for analysis with the Affymetrix® U133 Plus 2.0 array as described above. The data was analyzed by similar methods as described in Example 2 to identify differentially expressed genes.

As expected, many genes were differentially expressed between patients with acute infection and patients with aseptic loosening. 2451 genes showed a statistically different level of expression between the two groups when setting the false discovery rate to 5% and using rank products analysis (All raw data was sent to the to The Sir Henry Welcome Functional Genomics Facility & Bioinformatics Research Centre at Glasgow University).

Many of the genes identified in Example 1, were also identified as being differentially expressed between patients with acute infection and patients with aseptic loosening as described in this example. These results demonstrate that global markers specific for the underlying source of infection are produced by WBCs and have diagnostic value. All of the previously identified genes have potential diagnostic value in identifying clinical cases of infection. Genes that were differentially expressed in Example 1 and in the present example include, but are not limited to, skin-derived antileukoproteinase (SKALP) (PI3), interleukin-1 beta (IL 1 B), interleukin-8 (IL8), Interleukin-1 receptor-associated kinase 3 (IRAK3), CC chemokine ligand 3 (CCL3), CC chemokine ligand 4 (CCL4), superoxide dismutase 2 (SOD2), Nuclear Factor of Kappa light polypeptide gene enhancer in B-cells Inhibitor, Alpha (NFKBIA), Nijmegen breakage syndrome 1 (NBS1), tumor necrosis factor alpha-induced protein 6 (TNFAIP6), and plasminogen activator, urokinase (PLAU).

As expected from the results in Example 1, these results demonstrate that genes expressed from WBCs at the site of local inflammation have diagnostic value in terms of identifying the etiology of local inflammation. In other words, these results demonstrate that determining the level of expression of one or more genes in a clinical sample obtained from a site of local inflammation facilitates diagnosis of the source of that inflammation.

TABLE I

Genes whose Expression is Upregulated in Septic as compared to Aseptic Inflammation

| Rank | Affymetrix® U133A name | Fold Change | "Source" | Gene symbol |
|---|---|---|---|---|
| 1 | 203691_at | −19.55 | NM_002638 | PI3 |
| 2 | 206025_s_at | −13.37 | AW188198 | TNFAIP6 |
| 3 | 221345_at | −8.96 | NM_005306 | GPR43 |
| 4 | 202269_x_at | −9.81 | BC002666 | GBP1 |
| 5 | 204103_at | −13.31 | NM_002984 | CCL4 |
| 6 | 205114_s_at | −9.83 | NM_002983 | CCL3 |
| 7 | 205220_at | −6.94 | NM_006018 | HM74 |
| 8 | 41469_at | −10.79 | L10343 | PI3 |
| 9 | 36711_at | −9.5 | AL021977 | MAFF |
| 10 | 205479_s_at | −9.94 | NM_002658 | PLAU |
| 11 | 204224_s_at | −10.78 | NM_000161 | GCH1 |
| 12 | 215078_at | −9.41 | AL050388 | SOD2 |
| 13 | 203021_at | −10.19 | NM_003064 | SLPI |
| 14 | 218507_at | −8.6 | NM_013332 | HIG2 |
| 15 | 212657_s_at | −8.38 | U65590 | IL1RN |
| 16 | 202643_s_at | −6.63 | AI738896 | TNFAIP3 |
| 17 | 209969_s_at | −6.06 | BC002704 | STAT1 |
| 18 | 205067_at | −5.89 | NM_000576 | IL1B |
| 19 | 202193_at | −6.66 | NM_005569 | LIMK2 |
| 20 | 202270_at | −7.5 | NM_002053 | GBP1 |
| 21 | 202905_x_at | −6.62 | AI796269 | NBS1 |
| 22 | 39402_at | −5.36 | M15330 | IL1B |
| 23 | 206026_s_at | −6.08 | NM_007115 | TNFAIP6 |
| 24 | 202906_s_at | −7.46 | AF049895 | NBS1 |
| 25 | 211668_s_at | −7.87 | K03226 | PLAU |
| 26 | 201502_s_at | −6.66 | AI078167 | NFKBIA |
| 27 | 217299_s_at | −6.18 | AK001017 | NBS1 |
| 28 | 205040_at | −8.1 | NM_000607 | ORM1 |
| 29 | 205041_s_at | −8.1 | NM_000607 | ORM1 |
| 30 | 203470_s_at | −4.99 | AI433595 | PLEK |
| 31 | 216841_s_at | −4.44 | X15132 | SOD2 |
| 32 | 215223_s_at | −4.64 | W46388 | SOD2 |
| 33 | 211434_s_at | −6.39 | AF015524 | CCRL2 |
| 34 | 202887_s_at | −4.3 | NM_019058 | RTP801 |
| 35 | 214974_x_at | −4.5 | AK026546 | CXCL5 |
| 36 | 202644_s_at | −5.36 | NM_006290 | TNFAIP3 |
| 37 | 218280_x_at | −5.2 | NM_003516 | — |
| 38 | 207196_s_at | −5.4 | NM_006058 | TNIP1 |
| 39 | 209774_x_at | −6.47 | M57731 | CXCL2 |
| 40 | 213524_s_at | −4.47 | NM_015714 | G0S2 |
| 41 | 202638_s_at | −4.29 | NM_000201 | ICAM1 |
| 42 | 209288_s_at | −4.57 | AL136842 | CDC42EP3 |
| 43 | 205863_at | −4.37 | NM_005621 | S100A12 |
| 44 | 212090_at | −4.71 | AL571424 | GRINA |
| 45 | 205013_s_at | −6.03 | NM_000675 | ADORA2A |
| 46 | 218810_at | −4.96 | NM_025079 | FLJ23231 |
| 47 | 209050_s_at | −5.93 | AI421559 | RALGDS |
| 48 | 202581_at | −8.84 | NM_005346 | HSPA1A |
| 49 | 214290_s_at | −4 | AI313324 | — |
| 50 | 210582_s_at | −3.78 | AL117466 | LIMK2 |
| 51 | 207907_at | −5.1 | NM_003807 | TNFSF14 |
| 52 | 209051_s_at | −5.06 | AF295773 | RALGDS |
| 53 | 205476_at | −5.25 | NM_004591 | CCL20 |
| 54 | 201169_s_at | −4.62 | BG326045 | BHLHB2 |
| 55 | 201489_at | −5.1 | BC005020 | PPIF |
| 56 | 221920_s_at | −3.44 | BE677761 | MSCP |
| 57 | 206637_at | −4.81 | NM_014879 | GPR105 |
| 58 | 204351_at | −4.19 | NM_005980 | S100P |
| 59 | 207574_s_at | −3.81 | NM_015675 | GADD45B |
| 60 | 210845_s_at | −4.65 | U08839 | PLAUR |
| 61 | 213716_s_at | −4.18 | BF939675 | SECTM1 |
| 62 | 222088_s_at | −2.67 | AA778684 | SLC2A14 |
| 63 | 209038_s_at | −4.31 | AL579035 | EHD1 |
| 64 | 213638_at | −3.75 | AW054711 | RPEL1 |
| 65 | 212659_s_at | −3.49 | AW083357 | IL1RN |
| 66 | 218880_at | −4.58 | N36408 | FOSL2 |
| 67 | 222221_x_at | −3.74 | AY007161 | EHD1 |
| 68 | 202014_at | −4.22 | NM_014330 | PPP1R15A |
| 69 | 202531_at | −4.54 | NM_002198 | IRF1 |
| 70 | 207850_at | −4.67 | NM_002090 | CXCL3 |
| 71 | 209305_s_at | −3.94 | AF078077 | GADD45B |
| 72 | 202748_at | −3.6 | NM_004120 | GBP2 |
| 73 | 204908_s_at | −3.83 | NM_005178 | BCL3 |
| 74 | 200800_s_at | −4.78 | NM_005345 | HSPA1A |
| 75 | 204279_at | −3.68 | NM_002800 | PSMB9 |
| 76 | 209304_x_at | −3.43 | AF087853 | GADD45B |
| 77 | 202637_s_at | −3.5 | AI608725 | — |
| 78 | 218695_at | −4.77 | NM_019037 | RRP41 |
| 79 | 202284_s_at | −4.22 | NM_000389 | CDKN1A |
| 80 | 37028_at | −4.18 | U83981 | PPP1R15A |
| 81 | 220034_at | −3.63 | NM_007199 | IRAK3 |
| 82 | 209369_at | −4.09 | M63310 | ANXA3 |
| 83 | 208112_x_at | −3.48 | NM_006795 | EHD1 |
| 84 | 202307_s_at | −3.7 | NM_000593 | TAP1 |
| 85 | 204698_at | −3.33 | NM_002201 | ISG20 |
| 86 | 216243_s_at | −3.02 | BE563442 | IL1RN |
| 87 | 218999_at | −3.73 | NM_018295 | FLJ11000 |
| 88 | 201490_s_at | −3.14 | NM_005729 | PPIF |
| 89 | 206420_at | −3.33 | NM_005849 | IGSF6 |
| 90 | 205681_at | −2.92 | NM_004049 | BCL2A1 |
| 91 | 202192_at | −3.19 | NM_001124 | ADM |
| 92 | 202499_s_at | −2.34 | NM_006931 | SLC2A3 |
| 93 | 209039_x_at | −3.3 | AF001434 | EHD1 |
| 94 | 211924_s_at | −3.37 | AY029180 | PLAUR |
| 95 | 211883_x_at | −3.1 | M76742 | CEACAM1 |
| 96 | 217475_s_at | −2.73 | AC002073 | LIMK2 |
| 97 | 211725_s_at | −2.85 | BC005884 | BID |
| 98 | 216782_at | −2.75 | AK026679 | — |
| 99 | 209498_at | −3.12 | X16354 | CEACAM1 |
| 100 | 209037_s_at | −3.13 | AW182860 | EHD1 |
| 101 | 201810_s_at | −3.21 | AL562152 | SH3BP5 |
| 102 | 202426_s_at | −3.44 | BE675800 | RXRA |
| 103 | 58696_at | −3.85 | AL039469 | RRP41 |
| 104 | 33304_at | −3.05 | U88964 | ISG20 |
| 105 | 203045_at | −3.22 | NM_004148 | NINJ1 |
| 106 | 214657_s_at | −3.2 | AU134977 | — |
| 107 | 205270_s_at | −3.16 | NM_005565 | LCP2 |
| 108 | 214414_x_at | −3.19 | T50399 | HBA1 |
| 109 | 203137_at | −3.15 | NM_004906 | WTAP |
| 110 | 219938_s_at | −3.85 | NM_024430 | PSTPIP2 |
| 111 | 219669_at | −3.39 | NM_020406 | PRV1 |
| 112 | 211527_s_at | −2.67 | U64094 | IL1R2 |
| 113 | 200986_at | −4.04 | NM_000062 | SERPING1 |
| 114 | 202907_s_at | −3.23 | NM_002485 | NBS1 |
| 115 | 201649_at | −3.45 | NM_004223 | UBE2L6 |
| 116 | 201601_x_at | −2.62 | NM_003641 | IFITM1 |
| 117 | 203234_at | −3.05 | NM_003364 | UPP1 |
| 118 | 222303_at | −2.74 | AV700891 | ETS2 |
| 119 | 213812_s_at | −3.13 | AK024748 | CAMKK2 |
| 120 | 218833_s_at | −2.78 | NM_003498 | SNN |
| 121 | 204470_at | −2.93 | NM_001511 | CXCL1 |
| 122 | 217497_at | −2.97 | AW613387 | ECGF1 |
| 123 | 216236_s_at | −2.97 | AL110298 | SLC2A14 |
| 124 | 204070_at | −3.17 | NM_004585 | RARRES3 |
| 125 | 201473_at | −2.78 | NM_002229 | JUNB |
| 126 | 205269_at | −2.9 | AI123251 | LCP2 |
| 127 | 205322_s_at | −2.81 | AW182367 | — |
| 128 | 204951_at | −2.36 | NM_004310 | ARHH |
| 129 | 202498_s_at | −2.63 | BE550486 | SLC2A3 |
| 130 | 205403_at | −2.31 | NM_004633 | IL1R2 |
| 131 | 203471_s_at | −3.01 | NM_002664 | PLEK |
| 132 | 215977_x_at | −3.16 | X68285 | GK |
| 133 | 215966_x_at | −3.11 | AA292874 | GK |
| 134 | 211527_x_at | −3.15 | M27281 | VEGF |
| 135 | 217977_at | −2.57 | NM_016332 | SEPX1 |
| 136 | 204780_s_at | −2.28 | AA164751 | TNFRSF6 |
| 137 | 213700_s_at | −3.04 | AA554495 | PKM2 |
| 138 | 206765_at | −3.02 | AF153820 | KCNJ2 |
| 139 | 203936_s_at | −3.19 | NM_004994 | MMP9 |
| 140 | 207111_at | −2.42 | NM_001974 | EMR1 |
| 141 | 204748_at | −2.54 | NM_000963 | PTGS2 |
| 142 | 41386_i_at | −3.01 | AB002344 | KIAA0346 |
| 143 | 201294_s_at | −2.71 | N24643 | WSB1 |
| 144 | 200887_s_at | −3.36 | NM_007315 | STAT1 |
| 145 | 209367_at | −3.08 | AB002559 | STXBP2 |
| 146 | 91684_g_at | −2.81 | AI571298 | RRP41 |

TABLE I-continued

Genes whose Expression is Upregulated in Septic as compared to Aseptic Inflammation

| Rank | Affymetrix ® U133A name | Fold Change | "Source" | Gene symbol |
|---|---|---|---|---|
| 147 | 217167_x_at | −3.08 | AJ252550 | — |
| 148 | 202497_x_at | −2.91 | AI631159 | SLC2A3 |
| 149 | 208829_at | −2.35 | AF029750 | TAPBP |
| 150 | 209286_at | −2.52 | AI754416 | CDC42EP3 |
| 151 | 215760_s_at | −2.85 | AC005390 | KIAA0963 |
| 152 | 202807_s_at | −2.83 | NM_005488 | TOM1 |
| 153 | 205781_at | −2.6 | NM_004913 | C16orf7 |
| 154 | 214022_s_at | −2.27 | AA749101 | IFITM1 |
| 155 | 219622_at | −2.52 | NM_017817 | RAB20 |
| 156 | 204961_s_at | −2.89 | NM_000265 | NCF1 |
| 157 | 201362_at | −2.85 | AF205218 | IVNS1ABP |
| 158 | 210119_at | −2.31 | U73191 | KCNJ15 |
| 159 | 220712_at | −2.51 | NM_024984 | — |
| 160 | 210285_x_at | −2.4 | BC000383 | WTAP |
| 161 | 202464_s_at | −2.62 | NM_004566 | PFKFB3 |
| 162 | 217995_at | −2.71 | NM_021199 | SQRDL |
| 163 | 210512_s_at | −3.03 | AF022375 | VEGF |
| 164 | 209803_s_at | −4.1 | AF001294 | PHLDA2 |
| 165 | 209310_s_at | −2.76 | U25804 | CASP4 |
| 166 | 208092_s_at | −2.21 | NM_030797 | DKFZP566A1524 |
| 167 | 208992_s_at | −2.42 | BC000627 | STAT3 |
| 168 | 200666_s_at | −3.28 | NM_006145 | DNAJB1 |
| 169 | 200999_s_at | −2.76 | NM_006825 | CKAP4 |
| 170 | 213038_at | −2.29 | AL031602 | FLJ90005 |
| 171 | 214637_at | −1.98 | BG437034 | OSM |
| 172 | 208749_x_at | −2.35 | AF085357 | FLOT1 |
| 173 | 220193_at | −2.69 | NM_024676 | FLJ22938 |
| 174 | 211965_at | −2.33 | BE620915 | ZFP36L1 |
| 175 | 205205_at | −2.5 | NM_006509 | RELB |
| 176 | 204116_at | −2.62 | NM_000206 | IL2RG |
| 177 | 201811_x_at | −2.5 | NM_004844 | SH3BP5 |
| 178 | 207535_s_at | −2.5 | NM_002502 | NFKB2 |
| 179 | 218618_s_at | −2.93 | NM_022763 | FAD104 |
| 180 | 203068_at | −2.47 | NM_014851 | KIAA0469 |
| 181 | 201668_x_at | −2.35 | AW163148 | MARCKS |
| 182 | 209282_at | −2.68 | AF309082 | PRKD2 |
| 183 | 215498_s_at | −2.83 | AA780381 | MAP2K3 |
| 184 | 211745_x_at | −2.39 | BC005931 | HBA1 |
| 185 | 202121_s_at | −2.32 | NM_014453 | BC-2 |
| 186 | 204669_s_at | −2.6 | NM_007219 | RNF24 |
| 187 | 221477_s_at | −2.59 | BF575213 | SOD2 |
| 188 | 220000_at | −2.48 | NM_003830 | SIGLEC5 |
| 189 | 201631_s_at | −2.3 | NM_003897 | IER3 |
| 190 | 210142_x_at | −2.35 | AF117234 | FLOT1 |
| 191 | 213146_at | −2.48 | AA521267 | KIAA0346 |
| 192 | 209636_at | −2.68 | BC002844 | NFKB2 |
| 193 | 211316_x_at | −2.61 | AF009616 | CFLAR |
| 194 | 201772_at | −2.02 | NM_015878 | OAZIN |
| 195 | 212492_s_at | −2.47 | AW237172 | KIAA0876 |
| 196 | 214722_at | −2.88 | AW516297 | NOTCH2 |
| 197 | 203897_at | −2.33 | BE963444 | LOC57149 |
| 198 | 202102_s_at | −2.7 | BF718610 | BRD4 |
| 199 | 204494_s_at | −2.65 | AW516789 | DKFZP434H132 |
| 200 | 210563_x_at | −2.25 | U97075 | CFLAR |
| 201 | 205443_at | −2.26 | NM_003082 | SNAPC1 |
| 202 | AFFX-HUMISGF3A/M97935_MA_at | −2.09 | AFFX-HUMISGF3A/M97935_MA | — |
| 203 | AFFX-HUMISGF3A/M97935_3_at | −2.79 | AFFX-HUMISGF3A/M97935_3 | — |
| 204 | 221903_s_at | −2.51 | BE046443 | CYLD |
| 205 | 209458_x_at | −2.29 | AF105974 | HBA1 |
| 206 | 212723_at | −2.45 | AK021780 | PTDSR |
| 207 | 202510_s_at | −2.7 | NM_006291 | TNFAIP2 |
| 208 | 210511_s_at | −2.73 | M13436 | INHBA |
| 209 | 206877_at | −2.41 | NM_002357 | MAD |
| 210 | 216565_x_at | −2.35 | AL121994 | — |
| 211 | 201363_s_at | −2.38 | AB020657 | IVNS1ABP |
| 212 | 205193_at | −2.15 | NM_012323 | MAFF |
| 213 | 200648_s_at | −2.2 | NM_002065 | GLUL |
| 214 | 210513_s_at | −2.46 | AF091352 | VEGF |
| 215 | 212481_s_at | −2.11 | AI214061 | TPM4 |
| 216 | 211889_x_at | −2.35 | D12502 | CEACAM1 |
| 217 | 208991_at | −2.26 | AA634272 | STAT3 |
| 218 | 212902_at | −2.41 | BE645231 | SEC24A |
| 219 | 217414_x_at | −2.44 | V00489 | — |
| 220 | 212974_at | −2.35 | AI808958 | KIAA0870 |
| 221 | 202872_at | −2.27 | AW024925 | ATP6V1C1 |
| 222 | 219540_at | −2.28 | AU150728 | ZNF267 |
| 223 | 217202_s_at | −2.21 | U08626 | — |
| 224 | 215838_at | −1.86 | AF212842 | LIR9 |
| 225 | 203085_s_at | −2.16 | BC000125 | TGFB1 |
| 226 | 201329_s_at | −2.42 | NM_005239 | ETS2 |
| 227 | 217871_s_at | −2.8 | NM_002415 | MIF |
| 228 | 205323_s_at | −2.19 | NM_005955 | MTF1 |
| 229 | 205409_at | −2.11 | NM_005253 | FOSL2 |
| 230 | 209795_at | −2.89 | L07555 | CD69 |
| 231 | 201846_s_at | −2.17 | NM_012234 | RYBP |
| 232 | 211675_s_at | −2.71 | AB000463 | SH3BP2 |
| 233 | 211368_s_at | −2.53 | U13700 | CASP1 |
| 234 | 212226_s_at | −2.83 | AA628586 | PPAP2B |
| 235 | 202022_at | −2.39 | NM_005165 | ALDOC |
| 236 | 200799_at | −2.69 | NM_005345 | HSPA1A |
| 237 | 204490_s_at | −2.27 | M24915 | CD44 |
| 238 | 212722_s_at | −2.18 | AK021780 | PTDSR |
| 239 | 204435_at | −2.24 | NM_014778 | NUPL1 |
| 240 | 212203_x_at | −2.05 | BF338947 | IFITM3 |
| 241 | 211506_s_at | −1.99 | AF043337 | — |
| 242 | 203927_at | −2.91 | NM_004556 | NFKBIE |
| 243 | 207492_at | −2.51 | NM_025105 | NGLY1 |
| 244 | 205633_s_at | −2.52 | NM_000688 | ALAS1 |
| 245 | 212252_at | −2.07 | AA181179 | CAMKK2 |
| 246 | 215783_s_at | −2.68 | X14174 | ALPL |
| 247 | 208928_at | −2.28 | AF258341 | POR |
| 248 | 203175_at | −2.27 | NM_001665 | ARHG |
| 249 | 217985_s_at | −2.47 | AA102574 | BAZ1A |
| 250 | 200664_s_at | −2.6 | BG537255 | DNAJB1 |
| 251 | 211429_s_at | −2.39 | AF119873 | — |
| 252 | 201411_s_at | −2.36 | NM_017958 | PLEKHB2 |
| 253 | 200075_s_at | −2.44 | BC006249 | GUK1 |
| 254 | 201471_s_at | −2.42 | NM_003900 | SQSTM1 |
| 255 | 208751_at | −2.54 | BC001165 | NAPA |
| 256 | 201315_x_at | −1.82 | NM_006435 | IFITM2 |
| 257 | 220935_s_at | −2.37 | NM_018249 | CDK5RAP2 |
| 258 | 215719_x_at | −1.64 | X83493 | TNFRSF6 |
| 259 | 206011_at | −2.55 | AI719655 | CASP1 |
| 260 | 213817_at | −2.64 | AL049435 | — |
| 261 | 202205_at | −2.08 | NM_003370 | VASP |
| 262 | 211699_x_at | −2.11 | AF349571 | HBA1 |
| 263 | 212761_at | −2.11 | AI949687 | TCF7L2 |
| 264 | 200998_s_at | −2.33 | AW029619 | CKAP4 |
| 265 | 209116_x_at | −2.3 | M25079 | HBB |
| 266 | 218881_s_at | −2.1 | NM_024530 | FLJ23306 |
| 267 | 209354_at | −2.13 | BC002794 | TNFRSF14 |
| 268 | 205367_at | −2.66 | NM_020979 | APS |
| 269 | 208438_s_at | −2.18 | NM_005248 | FGR |
| 270 | 209545_s_at | −2.23 | AF064824 | RIPK2 |
| 271 | 208436_s_at | −2.42 | NM_004030 | IRF7 |
| 272 | 209761_s_at | −2.26 | AA969194 | SP110 |
| 273 | 220330_s_at | −2.46 | NM_022136 | SAMSN1 |
| 274 | 200632_s_at | −2.22 | NM_006096 | NDRG1 |
| 275 | 200822_x_at | −2.67 | NM_000365 | TPI1 |
| 276 | 209835_x_at | −2.22 | BC004372 | CD44 |
| 277 | 204018_x_at | −2.33 | NM_000558 | HBA1 |
| 278 | 38269_at | −2.19 | AL050147 | PRKD2 |
| 279 | 216252_x_at | −1.55 | Z70519 | TNFRSF6 |
| 280 | 219434_at | −1.85 | NM_018643 | TREM1 |
| 281 | 218611_at | −2.32 | NM_016545 | IER5 |
| 282 | 214211_at | −2.41 | AA083483 | FTH1 |
| 283 | 216316_x_at | −2 | X78713 | — |
| 284 | 218978_s_at | −2.34 | NM_018586 | MSCP |
| 285 | 214084_x_at | −2.41 | AW072388 | — |
| 286 | 209446_s_at | −2.6 | BC001743 | FLJ10803 |
| 287 | 209939_x_at | −2.08 | AF005775 | CFLAR |

TABLE I-continued

Genes whose Expression is Upregulated in Septic as compared to Aseptic Inflammation

| Rank | Affymetrix® U133A name | Fold Change | "Source" | Gene symbol |
|---|---|---|---|---|
| 288 | 210789_x_at | −2.28 | L00692 | CEACAM3 |
| 289 | 204265_s_at | −2.28 | NM_022107 | C6orf9 |
| 290 | 204166_at | −2.28 | NM_014963 | KIAA0963 |
| 291 | 219210_s_at | −2.18 | NM_016530 | LOC51762 |
| 292 | 202545_at | −2.19 | NM_006254 | PRKCD |
| 293 | 211696_x_at | −1.98 | AF349114 | HBB |
| 294 | 218088_s_at | −2.66 | NM_022157 | RRAGC |
| 295 | 206911_at | −2.07 | NM_005082 | ZNF147 |
| 296 | 204308_s_at | −2.48 | NM_014844 | KIAA0329 |
| 297 | 200649_at | −2.45 | BC002356 | NUCB1 |
| 298 | 213011_s_at | −2.39 | BF116254 | TPI1 |
| 299 | 202719_s_at | −2.06 | BC001451 | TES |
| 300 | 41387_r_at | −2.04 | AB002344 | KIAA0346 |
| 301 | 205026_at | −1.85 | NM_012448 | STAT5B |
| 302 | 221484_at | −1.97 | BF691447 | B4GALT5 |
| 303 | 205382_s_at | −1.86 | NM_001928 | DF |
| 304 | 209046_s_at | −2.22 | AB030710 | GABARAPL2 |
| 305 | 204924_at | −2.13 | NM_003264 | TLR2 |
| 306 | 207677_s_at | −2.22 | NM_013416 | NCF4 |
| 307 | 203508_at | −2.29 | NM_001066 | TNFRSF1B |
| 308 | 206245_s_at | −2.38 | NM_006469 | IVNS1ABP |
| 309 | 219947_at | −2.15 | NM_016184 | CLECSF6 |
| 310 | 209930_s_at | −2.48 | L13974 | NFE2 |
| 311 | 219202_at | −2.32 | NM_024599 | FLJ22341 |
| 312 | 204907_s_at | −2.17 | AI829875 | BCL3 |
| 313 | 208610_s_at | −2.04 | AI655799 | SRRM2 |
| 314 | 211661_x_at | −1.84 | M80436 | PTAFR |
| 315 | 201762_s_at | −2.06 | NM_002818 | PSME2 |
| 316 | 211302_s_at | −1.85 | L20966 | PDE4B |
| 317 | 212014_x_at | −2.13 | AI493245 | CD44 |
| 318 | 219357_at | −2.06 | NM_014027 | GTPBP1 |
| 319 | 203006_at | −2.09 | NM_005539 | INPP5A |
| 320 | 202833_s_at | −2.14 | NM_000295 | SERPINA1 |
| 321 | 203535_at | −1.68 | NM_002965 | S100A9 |
| 322 | 202856_s_at | −2.12 | NM_004207 | SLC16A3 |
| 323 | 36564_at | −1.92 | W27419 | FLJ90005 |
| 324 | 213988_s_at | −2.09 | BE971383 | SAT |
| 325 | 216915_s_at | −1.95 | S69182 | PTPN12 |
| 326 | 201192_s_at | −1.96 | NM_006224 | PITPN |
| 327 | 209457_at | −1.97 | U16996 | DUSP5 |
| 328 | 211806_s_at | −2.27 | D87291 | KCNJ15 |
| 329 | 204747_at | −1.95 | NM_001549 | IFIT4 |
| 330 | 219209_at | −2.13 | NM_022168 | MDA5 |
| 331 | 215101_s_at | −1.76 | BG166705 | CXCL5 |
| 332 | 201818_at | −2.03 | NM_024830 | FLJ12443 |
| 333 | 219082_at | −2.71 | NM_015944 | CGI-14 |
| 334 | 208918_s_at | −2.01 | AI334128 | FLJ13052 |
| 335 | 200646_s_at | −1.96 | NM_006184 | NUCB1 |
| 336 | 204157_s_at | −1.95 | NM_025164 | KIAA0999 |
| 337 | 209906_at | −2.02 | U62027 | C3AR1 |
| 338 | 214511_x_at | −1.79 | L03419 | FCGR1A |
| 339 | 204489_s_at | −2 | NM_000610 | CD44 |
| 340 | 214486_x_at | −2.14 | AF041459 | CFLAR |
| 341 | 218660_at | −1.96 | NM_003494 | DYSF |
| 342 | 209933_s_at | −2.04 | AF020314 | CMRF-35H |
| 343 | 203708_at | −1.73 | NM_002600 | PDE4B |
| 344 | 209355_s_at | −2.22 | AB000889 | PPAP2B |
| 345 | 214121_x_at | −1.95 | AA086229 | ENIGMA |
| 346 | 201942_s_at | −2.25 | D85390 | CPD |
| 347 | 207500_at | −2.13 | NM_004347 | CASP5 |
| 348 | 219593_at | −2 | NM_016582 | SLC15A3 |
| 349 | 212171_x_at | −2.02 | H95344 | VEGF |
| 350 | 211317_s_at | −1.84 | AF041461 | CFLAR |
| 351 | 208785_s_at | −1.95 | BE893893 | — |
| 352 | 217078_s_at | −2.02 | AJ010102 | CMRF-35H |
| 353 | 208637_x_at | −1.96 | BC003576 | ACTN1 |
| 354 | 221524_s_at | −1.78 | AF272036 | RRAGD |
| 355 | 210564_x_at | −1.85 | AF009619 | CFLAR |
| 356 | 209508_x_at | −2.12 | AF005774 | CFLAR |
| 357 | 203233_at | −1.74 | NM_000418 | IL4R |
| 358 | 202861_at | −1.92 | NM_002616 | PER1 |
| 359 | 205033_s_at | −2.17 | NM_004084 | DEFA1 |
| 360 | 206995_x_at | −1.85 | NM_003693 | SCARF1 |
| 361 | 221985_at | −1.89 | AW006750 | FLJ20059 |
| 362 | 202626_s_at | −1.92 | NM_002350 | LYN |
| 363 | 220404_at | −2.42 | NM_014076 | GPR97 |
| 364 | 216950_s_at | −2.09 | X14355 | FCGR1A |
| 365 | 209117_at | −1.93 | U79458 | WBP2 |
| 366 | 203591_s_at | −1.66 | NM_000760 | CSF3R |
| 367 | 211275_s_at | −1.56 | AF087942 | GYG |
| 368 | 221827_at | −2.17 | BE788439 | C20orf18 |
| 369 | 213418_at | −1.93 | NM_002155 | HSPA6 |
| 370 | 221764_at | −1.87 | AL574186 | MGC16353 |
| 371 | 214472_at | −2.08 | NM_003530 | HIST1H3D |
| 372 | 210629_x_at | −2.05 | AF000425 | LST1 |
| 373 | 206082_at | −1.85 | NM_006674 | HCP5 |
| 374 | 209970_x_at | −1.98 | M87507 | CASP1 |
| 375 | 202093_s_at | −1.89 | NM_019088 | PD2 |
| 376 | 208748_s_at | −1.65 | AA507012 | FLOT1 |
| 377 | 202509_s_at | −1.85 | AI862445 | TNFAIP2 |
| 378 | 207467_at | −1.52 | NM_002000 | FCAR |
| 379 | 217209_at | −1.85 | X16454 | — |
| 380 | 204581_at | −2.48 | NM_001771 | CD22 |
| 381 | 206278_at | −1.67 | D10202 | PTAFR |
| 382 | 205147_x_at | −2.26 | NM_000631 | NCF4 |
| 383 | 209193_at | −1.86 | M24779 | PIM1 |
| 384 | 201783_s_at | −1.86 | NM_021975 | RELA |
| 385 | 212496_s_at | −1.98 | BE256900 | KIAA0876 |
| 386 | 209020_at | −1.73 | AF217514 | C20orf111 |
| 387 | 212193_s_at | −1.78 | BG168720 | ZDHHC18 |
| 388 | 32069_at | −1.66 | AB014515 | N4BP1 |
| 389 | 214792_x_at | −2.18 | AI955119 | VAMP2 |
| 390 | 200629_at | −1.91 | NM_004184 | WARS |
| 391 | 211012_s_at | −1.93 | BC000080 | PML |
| 392 | 204053_x_at | −2.04 | U96180 | PTEN |
| 393 | 203925_at | −2.04 | NM_002061 | GCLM |
| 394 | 215499_at | −1.92 | AA780381 | MAP2K3 |
| 395 | 211862_x_at | −1.98 | AF015451 | CFLAR |
| 396 | 214014_at | −1.8 | W81196 | CDC42EP2 |
| 397 | 219774_at | −1.67 | NM_019044 | FLJ10996 |
| 398 | 200852_x_at | −1.9 | NM_005273 | GNB2 |
| 399 | 202146_at | −1.88 | AA747426 | IFRD1 |
| 400 | 201844_s_at | −1.79 | W84482 | RYBP |
| 401 | 200744_s_at | −1.91 | AI741124 | GNB1 |
| 402 | 210190_at | −1.61 | AF071504 | STX11 |
| 403 | 208052_x_at | −1.87 | NM_001815 | CEACAM3 |
| 404 | 203904_x_at | −1.82 | NM_002231 | KAI1 |
| 405 | 31845_at | −1.82 | U32645 | ELF4 |
| 406 | 203194_s_at | −1.94 | AA527238 | NUP98 |
| 407 | 212268_at | −1.84 | NM_030666 | SERPINB1 |
| 408 | 202842_s_at | −1.98 | AL080081 | DNAJB9 |
| 409 | 206359_at | −1.96 | BG035761 | SOCS3 |
| 410 | 202934_at | −1.83 | AI761561 | HK2 |
| 411 | 211307_s_at | −1.56 | U43677 | FCAR |
| 412 | 204232_at | −1.99 | NM_004106 | FCER1G |
| 413 | 202769_at | −1.89 | AW134535 | CCNG2 |
| 414 | 210449_x_at | −1.71 | AF100544 | MAPK14 |
| 415 | 200924_s_at | −2.23 | NM_002394 | SLC3A2 |
| 416 | 220319_s_at | −1.73 | NM_013262 | MIR |
| 417 | 210701_at | −1.99 | D85939 | CFDP1 |
| 418 | 204781_s_at | −2.01 | NM_000043 | TNFRSF6 |
| 419 | 208934_s_at | −2.25 | AF342815 | LGALS8 |
| 420 | 210029_at | −1.73 | M34455 | INDO |
| 421 | 215485_s_at | −1.71 | AA284705 | ICAM1 |
| 422 | 221385_at | −1.7 | NM_005305 | GPR42 |
| 423 | 214681_at | −2.08 | AI830490 | GK |
| 424 | 201353_s_at | −1.89 | AI653126 | BAZ2A |
| 425 | 213138_at | −1.81 | M62324 | MRF-1 |
| 426 | 219911_s_at | −1.84 | NM_016354 | SLC21A12 |
| 427 | 212007_at | −1.97 | AI927512 | UBXD2 |
| 428 | 201540_at | −1.91 | NM_001540 | HSPB1 |
| 429 | 210916_s_at | −1.93 | AF098641 | CD44 |
| 430 | 205159_at | −2.15 | AV756141 | CSF2RB |
| 431 | 205119_s_at | −1.55 | NM_002029 | FPR1 |
| 432 | 203882_at | −1.85 | NM_006084 | ISGF3G |
| 433 | 212041_at | −1.97 | AL566172 | ATP6V0D1 |

TABLE I-continued

Genes whose Expression is Upregulated in Septic as compared to Aseptic Inflammation

| Rank | Affymetrix® U133A name | Fold Change | "Source" | Gene symbol |
|---|---|---|---|---|
| 434 | 203574_at | −1.99 | NM_005384 | NFIL3 |
| 435 | 205483_s_at | −2.4 | NM_005101 | G1P2 |
| 436 | 204192_at | −2.01 | NM_001774 | CD37 |
| 437 | 219742_at | −1.58 | NM_030567 | MGC10772 |
| 438 | 205312_at | −2 | NM_003120 | SPI1 |
| 439 | 211582_x_at | −1.94 | AF000424 | LST1 |
| 440 | 200898_s_at | −1.88 | AK002091 | MGEA5 |
| 441 | 211366_x_at | −2 | U13698 | CASP1 |
| 442 | 205965_at | −1.78 | NM_006399 | BATF |
| 443 | 201625_s_at | −1.92 | BE300521 | INSIG1 |
| 444 | 201303_at | −1.63 | NM_014740 | DDX48 |
| 445 | 200966_x_at | −1.93 | NM_000034 | ALDOA |
| 446 | 201400_at | −1.88 | NM_002795 | PSMB3 |
| 447 | 206567_s_at | −1.71 | NM_016436 | C20orf104 |
| 448 | 211561_x_at | −1.69 | L35253 | MAPK14 |
| 449 | 218855_at | −2.25 | NM_016372 | TPRA40 |
| 450 | 201531_at | −2.09 | NM_003407 | ZFP36 |
| 451 | 202150_s_at | −1.71 | U64317 | NEDD9 |
| 452 | 211968_s_at | −1.53 | AI962933 | HSPCA |
| 453 | 221616_s_at | −1.76 | AF077053 | TAF9L |
| 454 | 209383_at | −1.73 | BC003637 | MARS |
| 455 | 117_at | −1.78 | X51757cds | HSPA6 |
| 456 | 213445_at | −1.73 | D63484 | KIAA0150 |
| 457 | 202671_s_at | −2.33 | NM_003681 | PDXK |
| 458 | 209791_at | −1.9 | AL049569 | PADI2 |
| 459 | 207667_s_at | −1.8 | NM_002756 | MAP2K3 |
| 460 | 208864_s_at | −1.65 | AF313911 | TXN |
| 461 | 211367_s_at | −2 | U13699 | CASP1 |
| 462 | 211160_x_at | −1.88 | M95178 | ACTN1 |
| 463 | 217232_x_at | −1.61 | AF059180 | — |
| 464 | 221978_at | −1.73 | BE138825 | HLA-F |
| 465 | 213593_s_at | −2.03 | AW978896 | TRA2A |
| 466 | 213607_x_at | −1.75 | BE551347 | — |
| 467 | 207275_s_at | −1.5 | NM_001995 | FACL2 |
| 468 | 202708_s_at | −2.01 | NM_003528 | HIST2H2BE |
| 469 | 204095_s_at | −1.62 | AL521391 | ELL |
| 470 | 202181_at | −2.01 | NM_014734 | KIAA0247 |
| 471 | 202241_at | −1.79 | NM_025195 | C8FW |
| 472 | 219257_s_at | −2.19 | NM_021972 | SPHK1 |
| 473 | 218943_s_at | −1.9 | NM_014314 | RIG-I |
| 474 | 214847_s_at | −1.93 | BG111168 | C6orf9 |
| 475 | 208499_s_at | −1.58 | NM_006260 | DNAJC3 |
| 476 | 201328_at | −1.79 | AL575509 | ETS2 |
| 477 | 219952_s_at | −1.77 | NM_020533 | MCOLN1 |
| 478 | 200730_s_at | −1.65 | BF576710 | PTP4A1 |
| 479 | 206491_s_at | −1.73 | NM_003827 | NAPA |
| 480 | 219403_s_at | −1.88 | NM_006665 | HPSE |
| 481 | 218154_at | −1.61 | NM_024736 | FLJ12150 |
| 482 | 215633_x_at | −1.84 | AV713720 | LST1 |
| 483 | 217492_s_at | −1.87 | AF023139 | PTENP1 |
| 484 | 219259_at | −1.76 | NM_022367 | FLJ12287 |
| 485 | 209272_at | −1.81 | AF045412 | NAB1 |
| 486 | 218404_at | −2.05 | NM_013322 | SNX10 |
| 487 | 220066_at | −1.8 | NM_022162 | CARD15 |
| 488 | 218673_s_at | −1.75 | NM_006395 | GSA7 |
| 489 | 219066_at | −1.7 | NM_021823 | MDS018 |
| 490 | 205180_s_at | −1.85 | NM_001109 | ADAM8 |
| 491 | 219359_at | −1.9 | NM_025092 | FLJ22635 |
| 492 | 201132_at | −1.77 | NM_019597 | HNRPH2 |
| 493 | 202855_s_at | −1.86 | AL513911 | SLC16A3 |
| 494 | 200766_at | −1.92 | NM_001909 | CTSD |
| 495 | 204970_s_at | −1.59 | NM_002359 | MAFG |
| 496 | 212769_at | −1.95 | AI567426 | TLE3 |
| 497 | 203922_s_at | −1.93 | AI308863 | CYBB |
| 498 | 201670_s_at | −1.81 | M68956 | MARCKS |
| 499 | 221962_s_at | −1.7 | AI829920 | UBE2H |
| 500 | 200704_at | −1.56 | AB034747 | LITAF |
| 501 | 209287_s_at | −1.84 | AF104253 | CDC42EP3 |
| 502 | 207113_s_at | −1.66 | NM_000594 | TNF |
| 503 | 210706_s_at | −2 | BC000213 | RNF24 |
| 504 | 221755_at | −1.99 | BG334196 | DKFZp762C186 |
| 505 | 203692_s_at | −1.68 | AI640363 | E2F3 |
| 506 | 206472_s_at | −1.92 | NM_005078 | TLE3 |
| 507 | 214574_x_at | −1.73 | NM_007161 | LST1 |
| 508 | 205844_at | −2.09 | NM_004666 | VNN1 |
| 509 | 214687_x_at | −1.91 | AK026577 | ALDOA |
| 510 | 203113_s_at | −1.63 | NM_001960 | EEF1D |
| 511 | 205349_at | −1.78 | NM_002068 | GNA15 |
| 512 | 214017_s_at | −1.82 | AA039439 | DHX34 |
| 513 | 214911_s_at | −1.71 | S78771 | BRD2 |
| 514 | 221617_at | −1.85 | AF077053 | TAF9L |
| 515 | 202910_s_at | −1.81 | NM_001784 | CD97 |
| 516 | 202140_s_at | −1.67 | NM_003992 | CLK3 |
| 517 | 203388_at | −1.6 | NM_004313 | ARRB2 |
| 518 | 213112_s_at | −1.82 | N30649 | SQSTM1 |
| 519 | 217966_s_at | −1.78 | NM_022083 | C1orf24 |
| 520 | 204269_at | −1.64 | NM_006875 | PIM2 |
| 521 | 206004_at | −1.56 | NM_003245 | TGM3 |
| 522 | 219690_at | −1.77 | NM_024660 | FLJ22573 |
| 523 | 201943_s_at | −1.89 | NM_001304 | CPD |
| 524 | 216650_at | −1.58 | AK026080 | SF3A1 |
| 525 | 208485_x_at | −1.87 | NM_003879 | CFLAR |
| 526 | 201168_x_at | −2 | NM_004309 | ARHGDIA |
| 527 | 35254_at | −1.71 | AB007447 | FLN29 |
| 528 | 203394_s_at | −1.55 | BE973687 | HES1 |
| 529 | 210773_s_at | −1.82 | U81501 | FPRL1 |
| 530 | 206576_s_at | −1.72 | NM_001712 | CEACAM1 |
| 531 | 212680_x_at | −1.7 | BE305165 | PPP1R14B |
| 532 | 200014_s_at | −1.69 | NM_004500 | HNRPC |
| 533 | 218302_at | −1.79 | NM_018468 | PEN2 |
| 534 | 214268_s_at | −1.89 | AL042220 | MTMR4 |
| 535 | 221571_at | −1.76 | AI721219 | TRAF3 |
| 536 | 218136_s_at | −1.81 | NM_018579 | MSCP |
| 537 | 209179_s_at | −1.72 | BC003164 | LENG4 |
| 538 | 202446_s_at | −1.69 | AI825926 | PLSCR1 |
| 539 | 200706_s_at | −1.75 | NM_004862 | LITAF |
| 540 | 91703_at | −1.95 | AA149545 | DKFZp762C186 |
| 541 | 204493_at | −1.61 | NM_001196 | BID |
| 542 | 203885_at | −1.74 | NM_014999 | RAB21 |
| 543 | 211133_x_at | −1.65 | AF009643 | LILRB3 |
| 544 | 211014_s_at | −1.77 | AF230410 | PML |
| 545 | 222024_s_at | −1.85 | AK022014 | AKAP13 |
| 546 | 205945_at | −1.83 | NM_000565 | IL6R |
| 547 | 214181_x_at | −1.77 | AI735692 | NCR3 |
| 548 | 200905_x_at | −1.59 | NM_005516 | HLA-E |
| 549 | 211711_s_at | −1.7 | BC005821 | PTEN |
| 550 | 210140_at | −1.7 | AF031824 | CST7 |
| 551 | 200733_s_at | −1.56 | U48296 | PTP4A1 |
| 552 | 215975_x_at | −1.74 | X68285 | GK |
| 553 | 206571_s_at | −1.83 | NM_004834 | MAP4K4 |
| 554 | 209017_s_at | −1.69 | BC001356 | IFI35 |
| 555 | 211135_x_at | −1.72 | AF009644 | LILRB3 |
| 556 | 204225_at | −1.99 | NM_006037 | MGC16025 |
| 557 | 211013_x_at | −1.61 | AF230411 | PML |
| 558 | 214508_x_at | −1.57 | U44836 | CREM |
| 559 | 221704_s_at | −1.63 | BC005882 | FLJ12750 |
| 560 | 203419_at | −1.84 | NM_014727 | MLL4 |
| 561 | 211581_x_at | −1.74 | AF000426 | LST1 |
| 562 | 211816_x_at | −1.51 | D87858 | FCAR |
| 563 | 215645_at | −1.54 | AF090883 | FLJ11286 |
| 564 | 209967_s_at | −1.71 | D14826 | CREM |
| 565 | 200065_s_at | −1.48 | AF052179 | ARF1 |
| 566 | 210625_s_at | −1.69 | AF009635 | LILRB3 |
| 567 | 205068_s_at | −1.79 | BE671084 | GRAF |
| 568 | 210772_at | −1.76 | M88107 | FPRL1 |
| 569 | 204769_s_at | −1.63 | M74447 | TAP2 |
| 570 | 217868_s_at | −1.67 | NM_016025 | DREV1 |
| 571 | 217817_at | −1.95 | BE891920 | ARPC4 |
| 572 | 211037_s_at | −1.78 | BC006309 | LENG4 |
| 573 | 215111_s_at | −1.66 | AK027071 | TSC22 |
| 574 | 209287_at | −1.69 | AI636233 | TMEM8 |
| 575 | 40420_at | −1.79 | AB015718 | STK10 |
| 576 | 203693_s_at | −1.81 | NM_001949 | E2F3 |
| 577 | 201926_s_at | −1.33 | BC001288 | DAF |
| 578 | 210610_at | −1.59 | M69176 | CEACAM1 |
| 579 | 218438_s_at | −1.63 | NM_025205 | EG1 |

TABLE I-continued

Genes whose Expression is Upregulated in Septic as compared to Aseptic Inflammation

| Rank | Affymetrix® U133A name | Fold Change | "Source" | Gene symbol |
|---|---|---|---|---|
| 580 | 200971_s_at | −1.61 | NM_014445 | SERP1 |
| 581 | 205645_at | −1.57 | NM_004726 | REPS2 |
| 582 | 204121_at | −1.67 | NM_006705 | GADD45G |
| 583 | 206707_x_at | −1.66 | NM_015864 | C6orf32 |
| 584 | 209919_x_at | −1.79 | L20490 | GGT1 |
| 585 | 207842_s_at | −1.68 | NM_007359 | MLN51 |
| 586 | 215148_s_at | −1.73 | AI141541 | APBA3 |
| 587 | 217941_s_at | −1.76 | NM_018695 | ERBB2IP |
| 588 | 204858_s_at | −1.63 | NM_001953 | ECGF1 |
| 589 | 211716_s_at | −1.9 | BC005851 | ARHGDIA |
| 590 | 210784_x_at | −1.56 | AF009634 | LILRB3 |
| 591 | AFFX-HUMISGF3A/M97935_5_at | −1.38 | AFFX-HUMISGF3A/M97935_5 | — |
| 592 | 201642_at | −1.72 | NM_005534 | IFNGR2 |
| 593 | 209216_at | −1.59 | BC000464 | JM5 |
| 594 | 201713_s_at | −1.61 | D42063 | RANBP2 |
| 595 | 211417_x_at | −1.7 | L20493 | GGT1 |
| 596 | 203616_at | −1.62 | NM_002690 | POLB |
| 597 | 202081_at | −1.7 | NM_004907 | ETR101 |
| 598 | 201963_at | −1.66 | NM_021122 | FACL2 |
| 599 | 214618_at | −1.62 | AF015452 | CFLAR |
| 600 | 209695_at | −1.58 | BC003105 | PTP4A3 |
| 601 | 210233_at | −1.62 | AF167343 | IL1RAP |
| 602 | 202874_s_at | −2.31 | NM_001695 | ATP6V1C1 |
| 603 | 205627_at | −1.56 | NM_001785 | CDA |
| 604 | 214446_at | −1.75 | NM_012081 | ELL2 |
| 605 | 36994_at | −1.76 | M62762 | ATP6V0C |
| 606 | 207338_s_at | −1.6 | NM_003454 | ZNF200 |
| 607 | 203528_at | −1.7 | NM_006378 | SEMA4D |
| 608 | 220023_at | −1.83 | NM_018690 | APOB48R |
| 609 | 205146_x_at | −1.64 | NM_004886 | APBA3 |
| 610 | 218310_at | −1.7 | NM_014504 | RABGEF1 |
| 611 | 208012_x_at | −1.83 | NM_004509 | SP110 |
| 612 | 203652_at | −1.6 | NM_002419 | MAP3K11 |
| 613 | 203749_s_at | −1.59 | AI806984 | RARA |
| 614 | 219862_s_at | −1.86 | NM_012336 | NARF |
| 615 | 214465_at | −1.55 | NM_000608 | ORM1 |
| 616 | 209762_x_at | −1.7 | AF280094 | SP110 |
| 617 | 202393_s_at | −1.86 | NM_005655 | TIEG |
| 618 | 211764_s_at | −1.86 | BC005980 | UBE2D1 |
| 619 | 204794_at | −1.74 | NM_004418 | DUSP2 |
| 620 | 212359_s_at | −1.58 | W89240 | KIAA0913 |
| 621 | 206513_at | −1.67 | NM_004833 | AIM2 |
| 622 | 221485_at | −1.57 | AL035683 | B4GALT5 |
| 623 | 219806_s_at | −1.65 | NM_020179 | FN5 |
| 624 | 212457_at | −1.57 | AL161985 | TFE3 |
| 625 | 211763_s_at | −1.6 | BC005979 | UBE2B |
| 626 | 209882_at | −1.69 | AF084462 | RIT1 |
| 627 | 202441_at | −1.58 | AL568449 | KEO4 |
| 628 | 201750_s_at | −1.61 | NM_001397 | ECE1 |
| 629 | 218586_at | −1.54 | NM_018270 | C20orf20 |
| 630 | 209850_s_at | −1.54 | BC005406 | CDC42EP2 |
| 631 | 201573_s_at | −1.81 | M75715 | ETF1 |
| 632 | 205425_at | −1.88 | NM_005338 | HIP1 |
| 633 | 221653_x_at | −1.57 | BC004395 | APOL2 |
| 634 | 213603_s_at | −1.63 | BE138888 | RAC2 |
| 635 | 203276_at | −1.79 | NM_005573 | LMNB1 |
| 636 | 205099_s_at | −1.7 | NM_001295 | CCR1 |
| 637 | 202941_at | −1.6 | NM_021074 | NDUFV2 |
| 638 | 202082_at | −1.59 | AV748469 | SEC14L1 |
| 639 | 203964_at | −1.96 | NM_004688 | NMI |
| 640 | 202618_s_at | −1.65 | L37298 | MECP2 |
| 641 | 201463_s_at | −1.6 | NM_006755 | TALDO1 |
| 642 | 208284_x_at | −1.7 | NM_013421 | GGT1 |
| 643 | 219394_at | −1.71 | NM_024419 | PGS1 |
| 644 | 215603_x_at | −1.47 | AI344075 | — |
| 645 | 200656_s_at | −1.74 | NM_000918 | P4HB |
| 646 | 212368_at | −1.83 | AA972711 | ZNF292 |
| 647 | 202625_at | −1.72 | AI356412 | LYN |
| 648 | 204243_at | −1.79 | NM_012421 | RLF |
| 649 | 205207_at | −1.6 | NM_000600 | IL6 |
| 650 | 209575_at | −1.61 | BC001903 | IL10RB |
| 651 | 217858_s_at | −1.58 | NM_016607 | ALEX3 |
| 652 | 214394_x_at | −1.56 | AI613383 | EEF1D |
| 653 | 213338_at | −1.7 | BF062629 | RIS1 |
| 654 | 217835_x_at | −1.57 | NM_018840 | C20orf24 |
| 655 | 203140_at | −1.75 | NM_001706 | BCL6 |
| 656 | 220470_at | −1.48 | NM_016526 | BET1L |
| 657 | 200954_at | −1.67 | NM_001694 | ATP6V0C |
| 658 | 207339_s_at | −1.73 | NM_002341 | LTB |
| 659 | 222025_s_at | −1.62 | AI991887 | OPLAH |
| 660 | 206203_s_at | −1.47 | NM_003122 | SPINK1 |
| 661 | 209451_at | −1.66 | U59863 | TANK |
| 662 | 218624_s_at | −1.58 | NM_023939 | MGC2752 |
| 663 | 220104_at | −1.56 | NM_020119 | ZAP |
| 664 | 207072_at | −1.41 | NM_003853 | IL18RAP |
| 665 | 211507_s_at | −1.57 | AF233437 | MTMR3 |
| 666 | 208881_x_at | −1.53 | BC005247 | IDI1 |
| 667 | 221680_s_at | −1.68 | AF147782 | ETV7 |
| 668 | 207248_at | −1.46 | NM_004895 | CIAS1 |
| 669 | 55705_at | −1.69 | W07773 | MGC16353 |
| 670 | 215732_s_at | −1.54 | AK023924 | DTX2 |
| 671 | 214737_x_at | −1.46 | AV725195 | HNRPC |
| 672 | 206607_at | −1.33 | NM_003855 | IL18R1 |
| 673 | 218279_s_at | −1.46 | BC001629 | — |
| 674 | 205568_at | −1.46 | NM_020980 | AQP9 |
| 675 | 218255_s_at | −1.58 | NM_022452 | FBS1 |
| 676 | 200881_s_at | −1.71 | NM_001539 | DNAJA1 |
| 677 | 207131_x_at | −1.79 | NM_013430 | GGT1 |
| 678 | 214753_at | −1.72 | AW084068 | CG005 |
| 679 | 212626_x_at | −1.43 | AA664258 | HNRPC |
| 680 | 208967_s_at | −1.52 | U39945 | AK2 |
| 681 | 209043_at | −1.66 | AF279899 | PNRC1 |
| 682 | 204958_at | −1.52 | NM_004073 | CNK |
| 683 | 218963_s_at | −1.84 | NM_015515 | KRT23 |
| 684 | 206503_x_at | −1.55 | NM_002675 | PML |
| 685 | 222175_s_at | −1.55 | AK000003 | PCQAP |
| 686 | 200814_at | −1.67 | NM_006263 | PSME1 |
| 687 | 202333_s_at | −1.69 | AA877765 | UBE2B |
| 688 | 201921_at | −1.64 | NM_004125 | GNG10 |
| 689 | 202083_s_at | −1.53 | AI017770 | SEC14L1 |
| 690 | 201693_s_at | −1.75 | AV733950 | EGR1 |
| 691 | 202537_s_at | −1.59 | AF151842 | DKFZP564O123 |
| 692 | 215884_s_at | −1.78 | AK001029 | — |
| 693 | 209654_s_at | −1.53 | AF323540 | APOL1 |
| 694 | 202841_s_at | −1.66 | NM_007346 | OGFR |
| 695 | 209238_at | −1.59 | BE966922 | STX3A |
| 696 | 214541_s_at | −1.59 | AF142418 | QKI |
| 697 | 203957_s_at | −1.81 | NM_005451 | ENIGMA |
| 698 | 222150_s_at | −1.53 | AK026747 | LOC54103 |
| 699 | 202382_s_at | −1.68 | NM_005471 | GNPI |
| 700 | 213142_x_at | −1.39 | AV700415 | LOC54103 |
| 701 | 213778_x_at | −1.56 | AI983201 | FANCA |
| 702 | 212689_s_at | −1.61 | AA524505 | JMJD1 |
| 703 | 201410_at | −1.68 | AI983043 | PLEKHB2 |
| 704 | 210118_s_at | −1.46 | M15329 | IL1A |
| 705 | 204601_at | −1.3 | NM_014664 | N4BP1 |
| 706 | 220585_at | −1.54 | NM_017555 | EGLN2 |
| 707 | 218085_at | −1.67 | NM_015961 | HSPC177 |
| 708 | 217591_at | −1.58 | BF725121 | SKIL |
| 709 | 203109_at | −1.59 | NM_003969 | UBE2M |
| 710 | 210362_x_at | −1.64 | AF230409 | PML |
| 711 | 202149_at | −1.57 | AL136139 | NEDD9 |
| 712 | 203853_s_at | −1.45 | NM_012296 | GAB2 |
| 713 | 212443_at | −1.68 | AB011112 | KIAA0540 |
| 714 | 202659_at | −1.44 | NM_002801 | PSMB10 |
| 715 | 207387_s_at | −1.18 | NM_000167 | GK |
| 716 | 204348_s_at | −1.52 | NM_013410 | AK3 |
| 717 | 207777_s_at | −1.54 | NM_007237 | SP140 |
| 718 | 200904_at | −1.46 | X56841 | HLA-E |
| 719 | 217986_s_at | −1.52 | NM_013448 | BAZ1A |
| 720 | 201940_at | −1.6 | AA897514 | CPD |
| 721 | 202684_s_at | −1.54 | AB020966 | RNMT |
| 722 | 204929_s_at | −1.66 | NM_006634 | VAMP5 |
| 723 | 202859_x_at | −1.4 | NM_000584 | IL8 |

TABLE I-continued

Genes whose Expression is Upregulated in Septic as compared to Aseptic Inflammation

| Rank | Affymetrix® U133A name | Fold Change | "Source" | Gene symbol |
|---|---|---|---|---|
| 724 | 203047_at | −1.71 | NM_005990 | STK10 |
| 725 | 210443_x_at | −1.59 | AF172452 | OGFR |
| 726 | 211799_x_at | −1.52 | U62824 | HLA-C |
| 727 | 207630_s_at | −1.62 | NM_001881 | CREM |
| 728 | 213596_at | −1.63 | AL050391 | CASP4 |
| 729 | 201556_at | −1.61 | BC002737 | VAMP2 |
| 730 | 201296_s_at | −1.72 | NM_015626 | WSB1 |
| 731 | 211865_s_at | −1.52 | AB013463 | FZR1 |
| 732 | 212561_at | −1.57 | AA349595 | RAB6IP1 |
| 733 | 204099_at | −1.56 | NM_003078 | SMARCD3 |
| 734 | 203530_s_at | −1.63 | NM_004604 | STX4A |
| 735 | 217436_x_at | −1.53 | M80469 | — |
| 736 | 205266_at | −1.53 | NM_002309 | LIF |
| 737 | 203028_s_at | −1.69 | NM_000101 | CYBA |
| 738 | 208685_x_at | −1.65 | AA902767 | BRD2 |
| 739 | 219183_s_at | −1.7 | NM_013385 | PSCD4 |
| 740 | 206247_at | −1.61 | NM_005931 | MICB |
| 741 | 217152_at | −1.5 | AK024136 | NCOR1 |
| 742 | 217962_at | −1.57 | NM_018648 | NOLA3 |
| 743 | 214919_s_at | −1.48 | R39094 | — |
| 744 | 200645_at | −1.66 | NM_007278 | GABARAP |
| 745 | 222326_at | −1.24 | AW973834 | — |
| 746 | 207713_s_at | −1.55 | NM_006462 | C20orf18 |
| 747 | 202688_at | −1.78 | NM_003810 | TNFSF10 |
| 748 | 201748_s_at | −1.46 | NM_002967 | SAFB |
| 749 | 219859_at | −1.61 | NM_014358 | CLECSF9 |
| 750 | 218130_at | −1.57 | NM_024510 | MGC4368 |
| 751 | 200078_s_at | −1.55 | BC005876 | ATP6V0B |
| 752 | 200808_s_at | −1.85 | NM_003461 | ZYX |
| 753 | 201170_s_at | −1.74 | NM_003670 | BHLHB2 |
| 754 | 204158_s_at | −1.4 | NM_006019 | TCIRG1 |
| 755 | 202574_s_at | −1.55 | NM_001319 | CSNK1G2 |
| 756 | 210754_s_at | −1.65 | M79321 | LYN |
| 757 | 209270_at | −1.4 | L25541 | LAMB3 |
| 758 | 204806_x_at | −1.52 | NM_018950 | HLA-F |
| 759 | 204615_x_at | −1.71 | NM_004508 | IDI1 |
| 760 | 209206_at | −1.56 | AV701283 | SEC22L1 |
| 761 | 203271_s_at | −1.54 | NM_005148 | UNC119 |
| 762 | 209398_at | −1.37 | BC002649 | HIST1H1C |
| 763 | 218319_at | −1.39 | NM_020651 | PELI1 |
| 764 | 213191_at | −1.42 | AF070530 | TRIF |
| 765 | 211969_at | −1.47 | BG420237 | HSPCA |
| 766 | 205003_at | −1.53 | NM_014705 | DOCK4 |
| 767 | 217422_s_at | −1.65 | X52785 | CD22 |
| 768 | 217911_s_at | −1.54 | NM_004281 | BAG3 |
| 769 | 209239_at | −1.55 | M55643 | NFKB1 |
| 770 | 209912_s_at | −1.56 | AI373854 | KIAA0415 |
| 771 | 204668_at | −1.36 | AL031695 | RNF24 |
| 772 | 208018_s_at | −1.68 | NM_002110 | HCK |
| 773 | 220467_at | −1.47 | NM_025032 | FLJ21272 |
| 774 | 220603_s_at | −1.35 | NM_018349 | FLJ11175 |
| 775 | 210538_s_at | −1.64 | U37546 | BIRC3 |
| 776 | 202734_at | −1.9 | NM_004240 | TRIP10 |
| 777 | 205585_at | −1.6 | NM_001987 | ETV6 |
| 778 | 201560_at | −1.42 | NM_013943 | CLIC4 |
| 779 | 205715_at | −1.4 | NM_004334 | BST1 |
| 780 | 221905_at | −1.56 | BF516433 | CYLD |
| 781 | 202255_s_at | −1.49 | NM_015556 | KIAA0440 |
| 782 | 201941_at | −1.69 | BE349147 | CPD |
| 783 | 214965_at | −1.52 | AF070774 | MGC26885 |
| 784 | 206756_at | −1.68 | NM_019886 | CHST7 |
| 785 | 204507_s_at | −1.61 | NM_000945 | PPP3R1 |
| 786 | 214083_at | −1.48 | AW772123 | PPP2R5C |
| 787 | 212540_at | −1.56 | BG476661 | CDC34 |
| 788 | 219763_at | −1.62 | NM_024820 | KIAA1608 |
| 789 | 221223_x_at | −1.48 | NM_013324 | CISH |
| 790 | 211605_s_at | −1.65 | U41742 | RARA |
| 791 | 202018_s_at | −1.51 | NM_002343 | LTF |
| 792 | 206697_s_at | −1.43 | NM_005143 | HP |
| 793 | 220941_s_at | −1.38 | NM_017447 | C21orf91 |
| 794 | 212900_at | −1.59 | AJ131244 | SEC24A |
| 795 | 209099_x_at | −1.55 | U73936 | JAG1 |
| 796 | 214693_x_at | −1.35 | BE732345 | NOTCH2 |
| 797 | 204804_at | −1.56 | NM_003141 | SSA1 |
| 798 | 202928_s_at | −1.56 | NM_024165 | PHF1 |
| 799 | 201186_at | −1.57 | NM_002337 | LRPAP1 |
| 800 | 210873_x_at | −1.65 | U03891 | APOBEC3A |
| 801 | 209192_x_at | −1.49 | BC000166 | HTATIP |
| 802 | 212242_at | −1.64 | AL565074 | TUBA1 |
| 803 | 202129_s_at | −1.7 | AW006290 | RIOK3 |
| 804 | 210951_x_at | −1.55 | AF125393 | RAB27A |
| 805 | 204118_at | −1.63 | NM_001778 | CD48 |
| 806 | 36_at | −1.39 | AF022991 | PER1 |
| 807 | 202391_at | −1.47 | NM_006317 | BASP1 |
| 808 | 203490_at | −1.5 | NM_001421 | ELF4 |
| 809 | 200055_at | −1.58 | NM_006284 | TAF10 |
| 810 | 210240_s_at | −1.45 | U20498 | CDKN2D |
| 811 | 219492_at | −1.67 | NM_012110 | CHIC2 |
| 812 | 211672_s_at | −1.56 | AF019888 | ARPC4 |
| 813 | 204293_at | −1.56 | NM_000199 | SGSH |
| 814 | 207592_s_at | −1.7 | NM_000480 | AMPD3 |
| 815 | 207419_s_at | −1.6 | NM_002872 | RAC2 |
| 816 | 211702_s_at | −1.51 | AF350251 | USP32 |
| 817 | 209477_at | −1.52 | BC000738 | EMD |
| 818 | 214590_s_at | −1.41 | AL545760 | UBE2D1 |
| 819 | 218728_s_at | −1.39 | NM_014184 | HSPC163 |
| 820 | 202687_s_at | −1.34 | U57059 | TNFSF10 |
| 821 | 212277_at | −1.69 | AB014547 | MTMR4 |
| 822 | 219625_s_at | −1.65 | NM_005713 | COL4A3BP |
| 823 | 221724_s_at | −1.54 | AF200738 | CLECSF6 |
| 824 | 212004_at | −1.53 | AL050028 | DKFZp566C0424 |
| 825 | 212947_at | −1.65 | AL031685 | SLC9A8 |
| 826 | 212286_at | −1.66 | AW572909 | KIAA0874 |
| 827 | AFFX-HUMISGF3A/M97935__MB_at | −1.49 | AFFX-HUMISGF3A/M97935__MB | — |
| 828 | 214866_at | −1.48 | X74039 | PLAUR |

TABLE II

Genes whose Expression is Downregulated in Septic as compared to Aseptic Inflammation

| Rank | Affymetrix® U133A name | Fold Change | "Source" | Gene symbol |
|---|---|---|---|---|
| 1 | 202345_s_at | 18.83 | NM_001444 | FABP5 |
| 2 | 201847_at | 7.21 | NM_000235 | LIPA |
| 3 | 206488_s_at | 10.7 | NM_000072 | CD36 |
| 4 | 201005_at | 7.21 | NM_001769 | CD9 |
| 5 | 201141_at | 6.93 | NM_002510 | GPNMB |
| 6 | 211734_s_at | 4.17 | BC005912 | FCER1A |
| 7 | 211719_x_at | 6.45 | BC005858 | FN1 |
| 8 | 216442_x_at | 6.45 | AK026737 | FN1 |
| 9 | 212192_at | 4.85 | AI718937 | LOC115207 |
| 10 | 204787_at | 5.16 | NM_007268 | Z39IG |
| 11 | 218559_s_at | 3.83 | NM_005461 | MAFB |
| 12 | 201212_at | 5.7 | D55696 | LGMN |
| 13 | 209555_s_at | 4.02 | M98399 | CD36 |
| 14 | 212464_s_at | 5.3 | X02761 | FN1 |
| 15 | 213872_at | 6.62 | BE465032 | C6orf62 |
| 16 | 219607_s_at | 6.17 | NM_024021 | MS4A4A |
| 17 | 210495_x_at | 5.4 | AF130095 | FN1 |
| 18 | 208146_s_at | 4.07 | NM_031311 | CPVL |
| 19 | 201279_s_at | 2.97 | BC003064 | DAB2 |
| 20 | 211571_s_at | 4.15 | D32039 | CSPG2 |
| 21 | 204121_at | 4.1 | NM_006895 | HNMT |
| 22 | 201278_at | 3.64 | N21202 | — |
| 23 | 202437_s_at | 3.45 | NM_000104 | CYP1B1 |
| 24 | 205695_at | 4.13 | NM_006843 | SDS |
| 25 | 210757_x_at | 2.46 | AF188298 | DAB2 |
| 26 | 203645_s_at | 3.39 | NM_004244 | CD163 |

TABLE II-continued

Genes whose Expression is Downregulated in Septic as compared to Aseptic Inflammation

| Rank | Affymetrix® U133A name | Fold Change | "Source" | Gene symbol |
|---|---|---|---|---|
| 27 | 212671_s_at | 4.04 | BG397856 | HLA-DQA1 |
| 28 | 215049_x_at | 3.36 | Z22969 | CD163 |
| 29 | 201280_s_at | 3.83 | NM_001343 | DAB2 |
| 30 | 201012_at | 3.01 | NM_000700 | ANXA1 |
| 31 | 202388_at | 2.81 | NM_002923 | RGS2 |
| 32 | 215646_s_at | 3.25 | R94644 | CSPG2 |
| 33 | 213566_at | 3.79 | NM_005615 | RNASE6 |
| 34 | 214770_at | 4.69 | AI299239 | MSR1 |
| 35 | 201273_s_at | 3.14 | NM_003133 | SRP9 |
| 36 | 200762_at | 3.59 | NM_001386 | DPYSL2 |
| 37 | 209728_at | 2.89 | BC005312 | HLA-DRB3 |
| 38 | 209377_s_at | 3.56 | AF274949 | HMGN3 |
| 39 | 200937_s_at | 3.35 | NM_000969 | RPL5 |
| 40 | 214085_x_at | 3.24 | AI912583 | HRB2 |
| 41 | 201302_at | 3.72 | NM_001153 | ANXA4 |
| 42 | 213619_at | 2.63 | AV753392 | HNRPH1 |
| 43 | 201947_s_at | 3.55 | NM_006431 | CCT2 |
| 44 | 201324_at | 3.65 | NM_001423 | EMP1 |
| 45 | 211991_s_at | 4.2 | M27487 | HLA-DPA1 |
| 46 | 201938_at | 3.09 | NM_004642 | CDK2AP1 |
| 47 | 209875_s_at | 2.52 | M83248 | SPP1 |
| 48 | 218723_s_at | 3.76 | NM_014059 | RGC32 |
| 49 | 201034_at | 3.06 | BE545756 | ADD3 |
| 50 | 202436_s_at | 2.22 | AU144855 | CYP1B1 |
| 51 | 219666_at | 3.07 | NM_022349 | MS4A6A |
| 52 | 213699_s_at | 3.06 | AA854017 | — |
| 53 | 218150_at | 2.64 | NM_012097 | ARL5 |
| 54 | 201339_s_at | 4.05 | NM_002979 | SCP2 |
| 55 | 203139_at | 2.44 | NM_004938 | DAPK1 |
| 56 | 201360_at | 3.08 | NM_000099 | CST3 |
| 57 | 201413_at | 2.34 | NM_004414 | HSD17B4 |
| 58 | 202591_s_at | 3.62 | NM_003143 | SSBP1 |
| 59 | 216834_at | 2.92 | S59049 | RGS1 |
| 60 | 210338_s_at | 3.38 | AB034951 | HSPA8 |
| 61 | 221019_at | 2.07 | NM_030781 | COLEC12 |
| 62 | 207761_s_at | 2.97 | NM_014033 | DKFZP586A0522 |
| 63 | 201068_s_at | 3.31 | NM_002803 | PSMC2 |
| 64 | 202207_at | 4.05 | BG435404 | ARL7 |
| 65 | 211675_s_at | 2.98 | AF054589 | HIC |
| 66 | 211733_x_at | 3.08 | BC005911 | SCP2 |
| 67 | 211784_s_at | 2.88 | BC006181 | SFRS1 |
| 68 | 202113_s_at | 3.38 | AF043453 | SNX2 |
| 69 | 204438_at | 3.29 | NM_002438 | MRC1 |
| 70 | 201137_s_at | 3.02 | NM_002121 | HLA-DPB1 |
| 71 | 201301_s_at | 3.36 | BC000182 | ANXA4 |
| 72 | 202546_at | 2.83 | NM_003761 | VAMP8 |
| 73 | 208638_at | 3.67 | BE910010 | ATP6V1C2 |
| 74 | 208923_at | 3.04 | BC005097 | CYFIP1 |
| 75 | 200034_s_at | 3.03 | NM_000970 | RPL6 |
| 76 | 202741_at | 2.46 | AA130247 | PRKACB |
| 77 | 200703_at | 3.23 | NM_003746 | DNCL1 |
| 78 | 218109_s_at | 3.32 | NM_022731 | FLJ14153 |
| 79 | 217478_s_at | 2.84 | X76775 | HLA-DMA |
| 80 | 213564_x_at | 3.01 | BE042354 | LDHB |
| 81 | 221773_at | 2.61 | AW575374 | ELK3 |
| 82 | 212586_at | 2.93 | AA195244 | CAST |
| 83 | 200016_x_at | 2.75 | NM_002136 | HNRPA1 |
| 84 | 211990_at | 2.89 | M27487 | HLA-DPA1 |
| 85 | 200657_at | 2.98 | NM_001152 | SLC25A5 |
| 86 | 200036_s_at | 3.04 | NM_007104 | RPL10A |
| 87 | 208627_s_at | 3 | BE966374 | NSEP1 |
| 88 | 200893_at | 2.7 | NM_004593 | SFRS10 |
| 89 | 214560_at | 2.07 | NM_002030 | FPRL2 |
| 90 | 213080_x_at | 3.01 | BF214492 | RPL5 |
| 91 | 200978_at | 3.05 | NM_005917 | MDH1 |
| 92 | 200082_s_at | 2.7 | AI805587 | RPS7 |
| 93 | 205292_s_at | 3.05 | NM_002137 | HNRPA2B1 |
| 94 | 202087_s_at | 2.97 | NM_001912 | CTSL |
| 95 | 200926_at | 2.64 | NM_001025 | RPS23 |
| 96 | 211972_x_at | 3.11 | AI953822 | RPLP0 |
| 97 | 201193_at | 2.72 | NM_005896 | IDH1 |
| 98 | 200074_s_at | 2.88 | U16738 | RPL14 |
| 99 | 208981_at | 2.33 | AA702701 | PECAM1 |
| 100 | 201944_at | 2.23 | NM_000521 | HEXB |
| 101 | 204006_s_at | 1.48 | NM_000570 | FCGR3A |
| 102 | 221476_s_at | 3.1 | AF279903 | RPL15 |
| 103 | 215691_x_at | 2.63 | AV702994 | — |
| 104 | 209200_at | 2.64 | AL536517 | MEF2C |
| 105 | 203741_s_at | 2.53 | NM_001114 | ADCY7 |
| 106 | 201754_at | 2.98 | NM_004374 | COX6C |
| 107 | 212907_at | 2.79 | AI972416 | SLC30A1 |
| 108 | 208983_s_at | 2.2 | M37780 | PECAM1 |
| 109 | 217802_s_at | 2.76 | NM_022731 | NUCKS |
| 110 | 202605_at | 2.9 | NM_000181 | GUSB |
| 111 | 211720_x_at | 3.1 | BC005863 | RPLP0 |
| 112 | 203305_at | 2.58 | NM_000129 | F13A1 |
| 113 | 200063_s_at | 2.64 | BC002398 | NPM1 |
| 114 | 201154_x_at | 2.85 | NM_000968 | RPL4 |
| 115 | 213738_s_at | 2.91 | AI587323 | ATP5A1 |
| 116 | 202377_at | 2.03 | AW026535 | LEPR |
| 117 | 211986_at | 2.9 | BG287862 | MGC5395 |
| 118 | 207507_s_at | 3.04 | NM_001689 | ATP5G3 |
| 119 | 204057_at | 1.81 | AI073984 | ICSBP1 |
| 120 | 201033_x_at | 2.93 | NM_001002 | RPLP0 |
| 121 | 201293_x_at | 2.87 | NM_021130 | PPIA |
| 122 | 207508_at | 3.14 | NM_001689 | ATP5G3 |
| 123 | 200705_s_at | 2.97 | NM_001959 | EEF1B2 |
| 124 | 208818_s_at | 3.34 | BC000419 | COMT |
| 125 | 217724_at | 2.64 | AF131807 | PAI-RBP1 |
| 126 | 200681_at | 2.52 | NM_006708 | GLO1 |
| 127 | 200750_s_at | 2.62 | AF054183 | RAN |
| 128 | 201952_at | 2.51 | AA156721 | ALCAM |
| 129 | 203104_at | 2.85 | NM_005211 | CSF1R |
| 130 | 219563_at | 1.86 | NM_024633 | C14orf139 |
| 131 | 213737_x_at | 2.11 | AI620911 | — |
| 132 | 208856_x_at | 2.84 | BC003655 | RPLP0 |
| 133 | 207168_s_at | 2.17 | NM_004893 | H2AFY |
| 134 | 213377_x_at | 2.85 | AI799007 | RPS12 |
| 135 | 221841_s_at | 2.41 | BF514079 | KLF4 |
| 136 | 201406_at | 2.55 | NM_021029 | RPL36A |
| 137 | 215091_s_at | 2.7 | BE542815 | GTF3A |
| 138 | 200033_at | 2.23 | NM_004396 | DDX5 |
| 139 | 213941_x_at | 2.63 | AI970731 | RPS7 |
| 140 | 201506_at | 2.69 | NM_000358 | TGFBI |
| 141 | 212426_s_at | 2.65 | BF033313 | YWHAQ |
| 142 | 202075_s_at | 2.12 | NM_006227 | PLTP |
| 143 | 200736_s_at | 2.3 | NM_000581 | GPX1 |
| 144 | 214141_x_at | 2.84 | BF033354 | SFRS7 |
| 145 | 213048_s_at | 2.45 | W26593 | SET |
| 146 | 211755_s_at | 2.66 | BC005960 | ATP5F1 |
| 147 | 204620_s_at | 2.07 | NM_004385 | CSPG2 |
| 148 | 221210_s_at | 1.98 | NM_030769 | NPL |
| 149 | 209191_at | 2.99 | BC002654 | TUBB-5 |
| 150 | 206682_at | 2.12 | NM_006344 | CLECSF13 |
| 151 | 218203_at | 2.7 | NM_013338 | ALG5 |
| 152 | 221802_s_at | 2.06 | AU157109 | KIAA1598 |
| 153 | 213356_x_at | 2.61 | AL568186 | HNRPA1 |
| 154 | 201427_s_at | 2.22 | NM_005410 | SEPP1 |
| 155 | 221731_x_at | 2.16 | BF218922 | CSPG2 |
| 156 | 213416_at | 2.01 | BG532690 | ITGA4 |
| 157 | 213979_s_at | 2.33 | BF984434 | CTBP1 |
| 158 | 201586_s_at | 2.81 | NM_005066 | SFPQ |
| 159 | 201398_s_at | 2.64 | BC000687 | TRAM1 |
| 160 | 211710_x_at | 2.82 | BC005817 | RPL4 |
| 161 | 212296_at | 2.82 | NM_005805 | PSMD14 |
| 162 | 214182_at | 2.12 | AA243143 | ARF6 |
| 163 | 201785_at | 2.14 | NM_002933 | RNASE1 |
| 164 | 201049_s_at | 2.81 | NM_022551 | RPS18 |
| 165 | 212010_s_at | 2.27 | AK025647 | H41 |
| 166 | 214167_s_at | 2.88 | AA555113 | — |
| 167 | 208627_s_at | 2.38 | M23254 | CAPN2 |
| 168 | 211072_x_at | 2.66 | BC006481 | K-ALPHA-1 |
| 169 | 209696_at | 2.5 | D26054 | FBP1 |
| 170 | 219725_at | 1.84 | NM_018965 | TREM2 |
| 171 | 204222_s_at | 2.41 | NM_006851 | GLIPR1 |
| 172 | 213655_at | 2.08 | AA502643 | YWHAE |

TABLE II-continued

Genes whose Expression is Downregulated in Septic as compared to Aseptic Inflammation

| Rank | Affymetrix® U133A name | Fold Change | "Source" | Gene symbol |
|---|---|---|---|---|
| 173 | 210139_s_at | 2.44 | L03203 | PMP22 |
| 174 | 201084_s_at | 2.6 | NM_014739 | BTF |
| 175 | 209480_at | 2.19 | M16276 | HLA-DQB1 |
| 176 | 200768_s_at | 2.56 | BC001686 | MAT2A |
| 177 | 220547_s_at | 2.68 | NM_019054 | MGC5560 |
| 178 | 217869_at | 2.69 | NM_016142 | HSD17B12 |
| 179 | 219279_at | 2.06 | NM_017718 | DOCK10 |
| 180 | 213537_at | 2.32 | AI128225 | HLA-DPA1 |
| 181 | 200023_s_at | 2.93 | NM_003754 | EIF3S5 |
| 182 | 200015_s_at | 2.15 | NM_004404 | NEDD5 |
| 183 | 203316_s_at | 2.54 | NM_003094 | SNRPE |
| 184 | 200004_at | 2.2 | NM_001418 | EIF4G2 |
| 185 | 215193_x_at | 2.74 | AJ297586 | HLA-DRB3 |
| 186 | 205898_at | 2.5 | U20350 | CX3CR1 |
| 187 | 203799_at | 2.6 | NM_014880 | DCL-1 |
| 188 | 208697_s_at | 2.39 | BC000734 | EIF3S6 |
| 189 | 211945_s_at | 2.45 | BG500301 | ITGB1 |
| 190 | 219358_s_at | 2.59 | NM_018404 | CENTA2 |
| 191 | 210982_s_at | 2.41 | M60333 | HLA-DRA |
| 192 | 200693_at | 2.54 | NM_006826 | YWHAQ |
| 193 | 218005_at | 2.51 | AA744771 | ZNF22 |
| 194 | 213801_x_at | 2.54 | AW304232 | LAMR1 |
| 195 | 206028_s_at | 2.24 | NM_006343 | MERTK |
| 196 | 217773_s_at | 2.44 | NM_002489 | NDUFA4 |
| 197 | 208654_s_at | 2.03 | BF669455 | CD164 |
| 198 | 201909_at | 2.24 | NM_001008 | RPS4Y |
| 199 | 205055_at | 1.89 | NM_002208 | ITGAE |
| 200 | 208073_x_at | 2.61 | NM_003316 | TTC3 |
| 201 | 200981_x_at | 1.97 | NM_016592 | GNAS |
| 202 | 218007_s_at | 2.54 | NM_015920 | RPS27L |
| 203 | 221452_s_at | 2.99 | NM_030969 | TMEM14B |
| 204 | 202544_at | 2.45 | NM_004124 | GMFB |
| 205 | 219452_at | 1.9 | NM_022355 | DPEP2 |
| 206 | 211985_s_at | 1.73 | AI653730 | CALM1 |
| 207 | 219032_x_at | 2.5 | NM_014322 | OPN3 |
| 208 | 211378_x_at | 2.64 | BC001224 | PPIA |
| 209 | 213047_x_at | 2.41 | AI278616 | SET |
| 210 | 200081_s_at | 2.45 | BE741754 | RPS6 |
| 211 | 201368_at | 1.89 | U07802 | — |
| 212 | 210027_s_at | 2.34 | M80261 | APEX1 |
| 213 | 211058_x_at | 2.59 | BC006379 | K-ALPHA-1 |
| 214 | 201338_x_at | 2.57 | NM_002097 | GTF3A |
| 215 | 201090_x_at | 2.59 | NM_006082 | K-ALPHA-1 |
| 216 | 201310_s_at | 2.09 | NM_004772 | C5orf13 |
| 217 | 210891_s_at | 1.94 | AF035737 | GTF2I |
| 218 | 208787_at | 2.67 | BC003375 | MRPL3 |
| 219 | 208669_s_at | 2.75 | AF109873 | CRI1 |
| 220 | 218589_at | 2.6 | NM_005767 | P2RY5 |
| 221 | 212638_s_at | 2.17 | BF131791 | WWP1 |
| 222 | 205882_x_at | 2.34 | AI818488 | ADD3 |
| 223 | 212188_at | 2.44 | AA551075 | LOC115207 |
| 224 | 34210_at | 2.38 | N90866 | CDW52 |
| 225 | 200838_at | 2.17 | NM_001908 | CTSB |
| 226 | 201590_x_at | 2.63 | NM_004039 | ANXA2 |
| 227 | 201092_at | 2.23 | NM_002893 | RBBP7 |
| 228 | 201153_s_at | 2.27 | NM_021038 | MBNL1 |
| 229 | 213646_x_at | 2.44 | BE300252 | K-ALPHA-1 |
| 230 | 200605_s_at | 2.35 | NM_002734 | PRKAR1A |
| 231 | 213503_x_at | 2.53 | BE908217 | ANXA2 |
| 232 | 211765_x_at | 2.73 | BC005982 | PPIA |
| 233 | 208628_s_at | 2.72 | BC002411 | NSEP1 |
| 234 | 204959_at | 2.65 | NM_002432 | MNDA |
| 235 | 201665_x_at | 2.55 | NM_001021 | RPS17 |
| 236 | 201795_at | 1.9 | NM_002296 | LBR |
| 237 | 212537_x_at | 2.14 | BE733979 | RPL17 |
| 238 | 200723_s_at | 2.45 | NM_005898 | M11S1 |
| 239 | 210427_x_at | 2.55 | BC001388 | ANXA2 |
| 240 | 209684_at | 2.23 | AL136924 | RIN2 |
| 241 | 219519_s_at | 2.44 | NM_023068 | SN |
| 242 | 203060_s_at | 2.43 | AF074331 | PAPSS2 |
| 243 | 200818_at | 2.56 | NM_001697 | ATP5O |
| 244 | 210895_s_at | 2.29 | L25259 | CD86 |
| 245 | 217757_at | 2.08 | NM_000014 | A2M |
| 246 | 212639_x_at | 2.48 | AL581768 | K-ALPHA-1 |
| 247 | 209031_at | 1.51 | AL519710 | IGSF4 |
| 248 | 201268_at | 2.34 | NM_002512 | NME2 |
| 249 | 201300_s_at | 2.2 | NM_000311 | PRNP |
| 250 | 218200_s_at | 2.54 | NM_004546 | NDUFB2 |
| 251 | 200839_s_at | 2.03 | NM_001908 | CTSB |
| 252 | 200038_s_at | 2.22 | NM_000985 | RPL17 |
| 253 | 202838_at | 2.51 | NM_000147 | FUCA1 |
| 254 | 201064_s_at | 2.63 | NM_003819 | PABPC4 |
| 255 | 220945_x_at | 1.8 | NM_018050 | FLJ10298 |
| 256 | 214548_x_at | 1.82 | AF064092 | GNAS |
| 257 | 211487_x_at | 2.62 | BC004886 | — |
| 258 | 211858_x_at | 1.88 | AF088184 | GNAS |
| 259 | 219777_at | 2.26 | NM_024711 | hIAN2 |
| 260 | 213831_at | 1.75 | X00452 | HLA-DQA1 |
| 261 | 200002_at | 2.23 | NM_007209 | RPL35 |
| 262 | 203381_s_at | 1.53 | N33009 | APOE |
| 263 | 200089_s_at | 2.62 | AI953886 | RPL4 |
| 264 | 212270_x_at | 2.05 | BG168283 | RPL17 |
| 265 | 208870_x_at | 2.28 | BC000931 | ATP5C1 |
| 266 | 209199_s_at | 2.21 | N22468 | MEF2C |
| 267 | 209312_x_at | 2.36 | U65585 | HLA-DRB3 |
| 268 | 212298_at | 1.52 | BE620457 | NRP1 |
| 269 | 215096_s_at | 2.64 | AU145746 | ESD |
| 270 | 202232_s_at | 2.42 | NM_006360 | GA17 |
| 271 | 200662_s_at | 2.13 | NM_014765 | TOMM20-PENDING |
| 272 | 208998_at | 2.37 | U94592 | UCP2 |
| 273 | 208858_s_at | 2.19 | BC004998 | MBC2 |
| 274 | 201973_s_at | 1.77 | AL550875 | — |
| 275 | 214042_s_at | 2.55 | AW071997 | — |
| 276 | 44790_s_at | 2.08 | AI129310 | C13orf18 |
| 277 | 201753_s_at | 2.14 | NM_019903 | ADD3 |
| 278 | 200873_s_at | 2.03 | NM_006585 | CCT8 |
| 279 | 200010_at | 2.51 | NM_000975 | RPL11 |
| 280 | 206991_s_at | 2.29 | NM_000579 | CCR5 |
| 281 | 208687_x_at | 2.64 | AF352832 | HSPA8 |
| 282 | 202602_s_at | 2.1 | NM_014500 | HTATSF1 |
| 283 | 212205_at | 1.75 | AA534860 | H2AV |
| 284 | 211939_x_at | 2.25 | X74070 | BTF3 |
| 285 | 212159_x_at | 2.35 | AI125280 | AP2A2 |
| 286 | 221775_x_at | 2.51 | BG152979 | — |
| 287 | 203663_s_at | 2.29 | NM_004255 | COX5A |
| 288 | 211978_s_at | 2.44 | AI708767 | PPIA |
| 289 | 201197_at | 2.35 | NM_001634 | AMD1 |
| 290 | 213366_x_at | 2.44 | AV711183 | ATP5C1 |
| 291 | 212661_x_at | 2.49 | BE731738 | — |
| 292 | 200780_x_at | 1.81 | NM_000516 | GNAS |
| 293 | 208768_x_at | 2.45 | D17652 | RPL22 |
| 294 | 200088_x_at | 2.45 | AK026491 | — |
| 295 | 201185_at | 2.38 | NM_002775 | PRSS11 |
| 296 | 218467_at | 2.25 | NM_020232 | HCCA3 |
| 297 | 211285_s_at | 2.58 | U84404 | UBE3A |
| 298 | 200595_s_at | 2.08 | NM_003750 | EIF3S10 |
| 299 | 203932_at | 2.41 | NM_002118 | HLA-DMB |
| 300 | 212273_x_at | 1.84 | AI591100 | GNAS |
| 301 | 201200_at | 1.95 | NM_003851 | CREG |
| 302 | 221691_x_at | 2.35 | AB042278 | NPM1 |
| 303 | 201515_s_at | 1.99 | NM_004622 | TSN |
| 304 | 212956_at | 2.16 | AI348094 | KIAA0882 |
| 305 | 205711_x_at | 2.47 | NM_005174 | ATP5C1 |
| 306 | 218224_at | 1.68 | NM_006029 | PNMA1 |
| 307 | 212248_at | 1.95 | AI886796 | LYRIC |
| 308 | 208894_at | 2.29 | M60334 | HLA-DRA |
| 309 | 209067_s_at | 2.33 | D89092 | HNRPDL |
| 310 | 221891_x_at | 2.79 | AA704004 | HSPA8 |
| 311 | 208833_s_at | 2.07 | AF119662 | E46L |
| 312 | 218139_s_at | 2.25 | NM_018229 | C14orf108 |
| 313 | 201030_x_at | 2.24 | NM_002300 | LDHB |
| 314 | 211747_s_at | 2.19 | BC005938 | LSM5 |
| 315 | 208944_at | 2.61 | D50683 | TGFBR2 |
| 316 | 220890_s_at | 1.83 | NM_016355 | DDX47 |
| 317 | 215450_at | 2.26 | W87901 | SNRPE |

TABLE II-continued

Genes whose Expression is Downregulated in Septic as compared to Aseptic Inflammation

| Rank | Affymetrix® U133A name | Fold Change | "Source" | Gene symbol |
|---|---|---|---|---|
| 318 | 201520_s_at | 2.6 | BF034561 | GRSF1 |
| 319 | 202206_at | 2.76 | AW450363 | ARL7 |
| 320 | 203382_s_at | 1.62 | NM_000041 | APOE |
| 321 | 215236_s_at | 2.04 | AV721177 | PICALM |
| 322 | 214323_s_at | 1.8 | N36842 | UPF3A |
| 323 | 200651_at | 2.37 | NM_006098 | GNB2L1 |
| 324 | 217870_at | 2.18 | NM_016308 | UMP-CMPK |
| 325 | 200909_s_at | 2.17 | NM_001004 | RPLP2 |
| 326 | 200028_s_at | 2.38 | NM_020151 | STARD7 |
| 327 | 212658_at | 2.17 | N66633 | LHFPL2 |
| 328 | 213347_x_at | 2.3 | AW132023 | RPS4X |
| 329 | 200061_s_at | 2.48 | BC000523 | RPS24 |
| 330 | 212131_at | 2.02 | BG054966 | DKFZP434D1335 |
| 331 | 213588_x_at | 2.44 | AA838274 | RPL14 |
| 332 | 217740_x_at | 2.3 | NM_000972 | RPL7A |
| 333 | 218577_at | 2.22 | NM_017768 | FLJ20331 |
| 334 | 213044_at | 2.28 | N22548 | ROCK1 |
| 335 | 201078_at | 1.84 | NM_004800 | TM9SF2 |
| 336 | 217873_at | 2.14 | NM_016289 | MO25 |
| 337 | 208319_s_at | 2.06 | NM_006743 | RBM3 |
| 338 | 212386_at | 1.99 | BF592782 | TCF4 |
| 339 | 204319_s_at | 1.92 | NM_002925 | RGS10 |
| 340 | 208674_x_at | 2.51 | BC002594 | DDOST |
| 341 | 214500_at | 2.06 | AF044286 | H2AFY |
| 342 | 202286_s_at | 1.15 | J04152 | TACSTD2 |
| 343 | 200099_s_at | 2.47 | AL356115 | — |
| 344 | 200872_at | 2.31 | NM_002966 | S100A10 |
| 345 | 221253_s_at | 2.25 | NM_030810 | TXNDC5 |
| 346 | 211656_x_at | 2.16 | M32577 | HLA-DQB1 |
| 347 | 221760_at | 2.2 | BG287153 | MAN1A1 |
| 348 | 200910_at | 2.36 | NM_005998 | CCT3 |
| 349 | 201330_at | 2.17 | NM_002887 | RARS |
| 350 | 216274_s_at | 2.07 | N99438 | SPC18 |
| 351 | 203153_at | 2.12 | NM_001548 | IFIT1 |
| 352 | 200858_s_at | 2.4 | NM_001012 | RPS8 |
| 353 | 202679_at | 2.24 | NM_000271 | NPC1 |
| 354 | 209389_x_at | 2.3 | M15887 | DBI |
| 355 | 212406_s_at | 2.06 | AB028973 | MYT1 |
| 356 | 202283_at | 1.68 | NM_002615 | SERPINF1 |
| 357 | 209251_x_at | 2.22 | BC004949 | TUBA6 |
| 358 | 201697_s_at | 1.97 | NM_001379 | DNMT1 |
| 359 | 212830_at | 1.87 | W68084 | EGFL5 |
| 360 | 212578_x_at | 2.31 | BF026595 | — |
| 361 | 212856_at | 2.16 | AB018310 | KIAA0767 |
| 362 | 218090_s_at | 2.21 | NM_018117 | WDR11 |
| 363 | 200911_s_at | 1.73 | NM_006283 | TACC1 |
| 364 | 211684_s_at | 2.46 | AF250307 | DNCI2 |
| 365 | 200030_s_at | 2.34 | NM_002635 | SLC25A3 |
| 366 | 212250_at | 2.06 | AV700332 | LYRIC |
| 367 | 221844_x_at | 2.23 | AV756161 | — |
| 368 | 200949_x_at | 2.48 | NM_001023 | RPS20 |
| 369 | 200754_x_at | 2.1 | NM_003016 | SFRS2 |
| 370 | 213084_x_at | 2.38 | BF125158 | RPL23A |
| 371 | 211984_at | 1.88 | AI653730 | CALM1 |
| 372 | 200915_x_at | 1.95 | NM_004986 | KTN1 |
| 373 | 202231_at | 2.17 | NM_006360 | GA17 |
| 374 | 212918_at | 2.07 | AI962943 | FLJ22028 |
| 375 | 201129_at | 2.42 | NM_006276 | SFRS7 |
| 376 | 208758_at | 2.07 | D89976 | ATIC |
| 377 | 221434_s_at | 2.37 | NM_031210 | DC50 |
| 378 | 210024_s_at | 2.41 | AB017644 | UBE2E3 |
| 379 | 208834_x_at | 2.38 | BC001865 | RPL23A |
| 380 | 217900_at | 2.18 | NM_018060 | FLJ10326 |
| 381 | 220495_s_at | 2.05 | NM_024715 | FLJ22625 |
| 382 | 211971_s_at | 1.89 | AI653608 | LRPPRC |
| 383 | 220960_x_at | 2.36 | NM_000983 | RPL22 |
| 384 | 219506_at | 1.76 | NM_024579 | FLJ23221 |
| 385 | 201112_s_at | 2.15 | NM_001316 | CSE1L |
| 386 | 212191_x_at | 2.04 | AW574664 | RPL13 |
| 387 | 209619_at | 2.18 | K01144 | CD74 |
| 388 | 200728_at | 1.89 | BE566290 | ACTR2 |
| 389 | 35974_at | 2.42 | U10485 | LRMP |
| 390 | 214003_x_at | 2.22 | BF184532 | RPS20 |
| 391 | 200631_s_at | 1.9 | NM_003011 | SET |
| 392 | 209397_at | 1.96 | BC000147 | ME2 |
| 393 | 201028_s_at | 2.2 | U82164 | CD99 |
| 394 | 204661_at | 2.23 | NM_001803 | CDW52 |
| 395 | 205987_at | 1.35 | NM_001765 | CD1C |
| 396 | 200809_x_at | 2.32 | NM_000976 | RPL12 |
| 397 | 217832_at | 2.15 | BE672181 | NSAP1 |
| 398 | 209861_s_at | 2.32 | U13261 | METAP2 |
| 399 | 201923_at | 2.17 | NM_006406 | PRDX4 |
| 400 | 212952_at | 2.01 | AA910371 | CALR |
| 401 | 209823_x_at | 2.28 | M17955 | HLA-DQB1 |
| 402 | 208825_x_at | 2.37 | U43701 | RPL23A |
| 403 | 211750_x_at | 2.09 | BC005946 | TUBA6 |
| 404 | 201619_at | 1.74 | NM_006793 | PRDX3 |
| 405 | 211666_x_at | 2.38 | L22453 | RPL3 |
| 406 | 213135_at | 1.92 | U90902 | TIAM1 |
| 407 | 214709_s_at | 1.92 | Z22551 | KTN1 |
| 408 | 204150_at | 2.02 | NM_015136 | STAB1 |
| 409 | 208517_x_at | 1.94 | NM_001207 | BTF3 |
| 410 | 215182_x_at | 1.39 | AL050122 | — |
| 411 | 203804_s_at | 1.79 | NM_006107 | LUC7A |
| 412 | 213274_s_at | 1.69 | AA020826 | CTSB |
| 413 | 201403_s_at | 2.25 | NM_004528 | MGST3 |
| 414 | 212482_at | 1.85 | BF671894 | FLJ13910 |
| 415 | 209974_s_at | 1.91 | AF047473 | BUB3 |
| 416 | 208306_x_at | 2.12 | NM_021983 | HLA-DRB3 |
| 417 | 212371_at | 1.9 | AL049397 | PNAS-4 |
| 418 | 212998_x_at | 1.9 | AI583173 | HLA-DQB2 |
| 419 | 200025_s_at | 2.26 | NM_000988 | RPL27 |
| 420 | 203156_at | 1.64 | NM_016248 | AKAP11 |
| 421 | 208703_s_at | 1.6 | BG427393 | APLP2 |
| 422 | 220526_s_at | 2.38 | NM_017971 | MRPL20 |
| 423 | 211779_x_at | 2.11 | BC006155 | AP2A2 |
| 424 | 221748_s_at | 2.02 | AL046979 | TNS |
| 425 | 221475_s_at | 2.18 | NM_002948 | RPL15 |
| 426 | 212168_at | 2.14 | AL514547 | CPNE1 |
| 427 | 217906_at | 2.02 | NM_014315 | KLHDC2 |
| 428 | 212036_s_at | 2.28 | AW152664 | PNN |
| 429 | 204141_at | 2.2 | NM_001069 | TUBB |
| 430 | 203403_s_at | 2.25 | NM_005977 | RNF6 |
| 431 | 202396_at | 1.62 | NM_006706 | TCERG1 |
| 432 | 200740_s_at | 2.37 | NM_006936 | SMT3H1 |
| 433 | 201784_s_at | 1.97 | NM_014267 | SMAP |
| 434 | 204616_at | 2.35 | NM_006002 | UCHL3 |
| 435 | 205466_s_at | 2.02 | NM_005114 | HS3ST1 |
| 436 | 209154_at | 1.85 | AF234997 | TIP-1 |
| 437 | 202502_at | 1.75 | NM_000016 | ACADM |
| 438 | 216241_s_at | 2.07 | X57198 | TCEA1 |
| 439 | 211070_x_at | 2.39 | BC006466 | DBI |
| 440 | 201254_x_at | 2.37 | NM_001010 | RPS6 |
| 441 | 210889_s_at | 1.89 | M31933 | FCGR2B |
| 442 | 212904_at | 2.12 | AB033011 | KIAA1185 |
| 443 | 210645_s_at | 2.1 | D83077 | TTC3 |
| 444 | 200963_x_at | 1.97 | NM_000993 | RPL31 |
| 445 | 213687_s_at | 2.22 | BE968801 | RPL35A |
| 446 | 216640_s_at | 2.05 | AK026926 | — |
| 447 | 221565_s_at | 1.83 | BC000039 | LOC51063 |
| 448 | 38487_at | 1.79 | D87433 | STAB1 |
| 449 | 204342_at | 2.24 | NM_013386 | DKFZp586G0123 |
| 450 | 219471_at | 2.09 | NM_025113 | C13orf18 |
| 451 | 217719_at | 2.22 | NM_016091 | EIF3S6IP |
| 452 | 209240_at | 1.69 | AF070560 | OGT |
| 453 | 210149_s_at | 2.14 | AF061735 | ATP5H |
| 454 | 200008_s_at | 1.93 | D13988 | GDI2 |
| 455 | 217491_s_at | 2.07 | AF042165 | COX7C |
| 456 | 200834_s_at | 1.97 | NM_001024 | RPS21 |
| 457 | 200933_x_at | 2.37 | NM_001007 | RPS4X |
| 458 | 213642_at | 1.75 | BE312027 | RPL27 |
| 459 | 200804_s_at | 1.97 | AL031681 | SFRS6 |
| 460 | 218263_s_at | 1.83 | NM_021211 | LOC58486 |
| 461 | 208997_s_at | 2.09 | U82819 | UCP2 |
| 462 | 221726_at | 1.9 | BE250348 | RPL22 |
| 463 | 211073_x_at | 2.24 | BC006483 | RPL3 |

TABLE II-continued

Genes whose Expression is Downregulated in Septic as compared to Aseptic Inflammation

| Rank | Affymetrix ® U133A name | Fold Change | "Source" | Gene symbol |
|---|---|---|---|---|
| 464 | 206710_s_at | 1.77 | NM_012307 | EPB41L3 |
| 465 | 200943_at | 2.32 | NM_004965 | HMGN1 |
| 466 | 201687_s_at | 1.94 | NM_006595 | API5 |
| 467 | 201217_x_at | 2.35 | NM_000967 | RPL3 |
| 468 | 202088_at | 1.97 | AI635449 | SLC39A6 |
| 469 | 201327_s_at | 1.91 | NM_001762 | CCT6A |
| 470 | 207040_s_at | 2.01 | NM_003932 | ST13 |
| 471 | 214830_at | 1.99 | AI537540 | SLC38A6 |
| 472 | 201312_s_at | 2.16 | NM_003022 | SH3BGRL |
| 473 | 202428_x_at | 2.29 | NM_020548 | DBI |
| 474 | 218802_at | 2.21 | NM_017918 | FLJ20647 |
| 475 | 203012_x_at | 2.18 | NM_000984 | RPL23A |
| 476 | 216342_x_at | 2.26 | AL121916 | — |
| 477 | 203534_at | 1.83 | NM_014462 | LSM1 |
| 478 | 212585_at | 2.75 | BF970829 | OSBPL8 |
| 479 | 209118_s_at | 2.11 | AF141347 | TUBA3 |
| 480 | 209092_s_at | 2.25 | AF061730 | CGI-150 |
| 481 | 212888_at | 1.7 | BG109746 | DICER1 |
| 482 | 204670_x_at | 2.12 | NM_002125 | HLA-DRB3 |
| 483 | 202077_at | 2.13 | NM_005003 | NDUFAB1 |
| 484 | 213864_s_at | 1.69 | AI985751 | NAP1L1 |
| 485 | 201444_s_at | 1.87 | NM_005765 | ATP6AP2 |
| 486 | 208929_x_at | 1.96 | BC004954 | RPL13 |
| 487 | 208775_at | 1.51 | D89729 | XPO1 |
| 488 | 200763_s_at | 2.05 | NM_001003 | RPLP1 |
| 489 | 201946_s_at | 2.21 | AL545982 | CCT2 |
| 490 | 218041_x_at | 1.97 | NM_018573 | SLC38A2 |
| 491 | 201325_s_at | 1.69 | NM_001423 | EMP1 |
| 492 | 217945_at | 1.94 | NM_025238 | BTBD1 |
| 493 | 204619_s_at | 1.75 | BF590263 | CSPG2 |
| 494 | 217362_x_at | 1.99 | AF005487 | HLA-DRB3 |
| 495 | 202351_at | 2.17 | AI093579 | ITGAV |
| 496 | 202381_at | 2.02 | NM_003816 | ADAM9 |
| 497 | 220044_x_at | 1.81 | NM_016424 | LUC7A |
| 498 | 203547_at | 2.24 | U47924 | CD4 |
| 499 | 201071_x_at | 2.44 | NM_012433 | SF3B1 |
| 500 | 206978_at | 1.78 | NM_000647 | CCR2 |
| 501 | 211185_s_at | 2.14 | AF130099 | FLJ14753 |
| 502 | 208617_s_at | 1.82 | AF208850 | PTP4A2 |
| 503 | 200726_at | 2.04 | NM_002710 | PPP1CC |
| 504 | 208982_at | 1.66 | AW574504 | PECAM1 |
| 505 | 212039_x_at | 2.37 | BG339228 | RPL3 |
| 506 | 200091_s_at | 2.04 | AA888388 | RPS25 |
| 507 | 217846_at | 2.24 | NM_005051 | QARS |
| 508 | 212560_at | 2.16 | AV728268 | SORL1 |
| 509 | 203473_at | 1.67 | NM_007256 | SLC21A9 |
| 510 | 200955_at | 2.14 | NM_006839 | IMMT |
| 511 | 205988_at | 1.68 | NM_003874 | CD84 |
| 512 | 212266_s_at | 1.81 | AW084582 | SFRS5 |
| 513 | 212515_s_at | 2.24 | BG492602 | DDX3X |
| 514 | 219065_s_at | 1.78 | NM_015955 | CGI-27 |
| 515 | 202469_s_at | 1.95 | AU149367 | CPSF6 |
| 516 | 221751_at | 1.74 | AL565516 | PANK3 |
| 517 | 217933_s_at | 1.92 | NM_015907 | LAP3 |
| 518 | 203485_at | 1.93 | NM_021136 | RTN1 |
| 519 | 218191_s_at | 2.23 | NM_018368 | FLJ11240 |
| 520 | 208635_x_at | 1.88 | BF976260 | NACA |
| 521 | 204892_x_at | 1.93 | NM_001402 | EEF1A1 |
| 522 | 203721_s_at | 2.07 | NM_016001 | CGI-48 |
| 523 | 212640_at | 1.8 | AV712602 | LOC201562 |
| 524 | 201029_s_at | 2.06 | NM_002414 | CD99 |
| 525 | 211697_x_at | 1.39 | AF349314 | LOC56902 |
| 526 | 201065_s_at | 2.09 | NM_001518 | GTF2I |
| 527 | 213923_at | 1.92 | AW005535 | RAP2B |
| 528 | 200024_at | 2.1 | NM_001009 | RPS5 |
| 529 | 202378_s_at | 1.73 | NM_017526 | LEPR |
| 530 | 218856_at | 2.13 | NM_016629 | TNFRSF21 |
| 531 | 208816_x_at | 2.27 | M62898 | — |
| 532 | 201672_s_at | 2.1 | NM_005151 | USP14 |
| 533 | 214047_s_at | 1.5 | AI913365 | MBD4 |
| 534 | 212042_x_at | 2.12 | BG389744 | RPL7 |
| 535 | 211742_s_at | 1.75 | BC005926 | EVI2B |

Modifications and variations of the methods and compositions described herein will be obvious to those skilled in the art and are intended to come within the scope of the appended claims. The teachings of the references cited herein are specifically incorporated by reference.

I claim:

1. A method of diagnosing the source of local inflammation comprising:
   determining the expression of one or more genes from a cell, or proteins encoded thereby, from a clinical synovial fluid sample obtained from a site of local inflammation, and comparing the expression of these genes with their expression in known control samples from a comparable site without local inflammation to determine if the site is infected, wherein levels of expression of one or more genes, or proteins encoded thereby, indicative of bacterial infection, from the site of local inflammation are altered by at least two fold by bacterial infection.

2. The method of claim 1 wherein the gene expression is detected by examining nucleic acid expression.

3. The method of claim 1 wherein the gene expression is detected by examining protein expression.

4. The method of claim 1 wherein expression of a gene is determined by assaying for an mRNA transcribed from the gene or a protein translated from an mRNA transcribed from the gene.

5. The method of claim 1 wherein the sample is synovial fluid from the knee.

6. The method of claim 1 wherein the sample consists predominantly of neutrophils or other white cells.

7. The method of claim 1 wherein the genes are analyzed on a microarray.

8. The method of claim 1 further comprising comparing the measured levels of expression or protein with levels from controls obtained from individuals with confirmed infection.

9. The method of claim 1 wherein the synovial fluid samples and controls are obtained from individuals with confirmed inflammation due to gout or autoimmune disease.

10. The method of claim 1 wherein the expression is compared by comparing protein expressed from the genes.

11. The method of claim 1 wherein the genes are selected from the group consisting of PI3, TNFAIP6, GPR43, GBP1, CCL4, CCL3, HM74, MAFF, PLAU, GCH1, SOD2, SLPI, HIG2, IL1RN, FABP5, LIPA, CD36, CD9, GPNMB, FCER1A, FN1, LOC115207, Z39 IG, MAFB, LGMN, CD36, FN1, C6orf62, and MS4A4A.

12. The method of claim 1 wherein the expression or protein levels are three fold different.

13. The method of claim 1 wherein the expression or protein levels are five fold different.

14. The method of claim 1 wherein the expression or protein levels are ten fold different.

15. The method of claim 1 wherein the proteins are selected from the group consisting of skin-derived antileukoproteinase (SKALP) (PI3), interleukin-1beta (IL1B), interleukin-8 (IL8), Interleukin-1 receptor-associated kinase 3 (IRAK3), CC chemokine ligand 3 (CCL3), CC chemokine ligand 4 (CCL4), superoxide dismutase 2 (SOD2), Nuclear Factor of Kappa light polypeptide gene enhancer in B-cells Inhibitor, Alpha (NFKBIA), Nijmegen breakage syndrome 1 (NBS 1), tumor necrosis factor alpha-induced protein 6 (TNFAIP6), and plasminogen activator, urokinase (PLAU).

* * * * *